United States Patent
Itkowitz et al.

(10) Patent No.: US 10,548,459 B2
(45) Date of Patent: Feb. 4, 2020

(54) SYSTEMS AND METHODS FOR CONTROL OF IMAGING INSTRUMENT ORIENTATION

(71) Applicant: INTUITIVE SURGICAL OPERATIONS, INC, Sunnyvale, CA (US)

(72) Inventors: Brandon D. Itkowitz, Sunnyvale, CA (US); Ian E. McDowall, Woodside, CA (US); Thomas R. Nixon, San Jose, CA (US); Bruce M. Schena, Menlo Park, CA (US); Niels Smaby, Palo Alto, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 226 days.

(21) Appl. No.: 15/262,932

(22) PCT Filed: Mar. 17, 2015

(86) PCT No.: PCT/US2015/021110
§ 371 (c)(1),
(2) Date: Sep. 12, 2016

(87) PCT Pub. No.: WO2015/142957
PCT Pub. Date: Sep. 24, 2015

(65) Prior Publication Data
US 2017/0188792 A1 Jul. 6, 2017

Related U.S. Application Data

(60) Provisional application No. 61/954,338, filed on Mar. 17, 2014.

(51) Int. Cl.
*A61B 1/00* (2006.01)
*A61B 34/30* (2016.01)
(Continued)

(52) U.S. Cl.
CPC ........ *A61B 1/00006* (2013.01); *A61B 1/0005* (2013.01); *A61B 1/00009* (2013.01);
(Continued)

(58) Field of Classification Search
CPC ............ A61B 1/00006; A61B 1/00009; A61B 1/0005; A61B 1/00179; A61B 1/04;
(Continued)

(56) References Cited

U.S. PATENT DOCUMENTS 4,710,002 A * 12/1987 Pomerantzeff ......... A61B 3/132
351/205
5,099,850 A * 3/1992 Matsui ............... A61B 1/00179
600/109

(Continued)

FOREIGN PATENT DOCUMENTS

CN 101014281 A 8/2007
CN 101056576 A 10/2007
(Continued)

OTHER PUBLICATIONS

Extended European Search Report for Application No. 15764786.8, dated Oct. 19, 2017, 8 pages.
(Continued)

*Primary Examiner* — John P Leubecker
*Assistant Examiner* — Shankar Raj Ghimire
(74) *Attorney, Agent, or Firm* — Haynes and Boone, LLP

(57) ABSTRACT

A medical imaging system comprises a teleoperational assembly and a processing unit configured for receiving a roll position indicator for an imaging instrument coupled to the teleoperational assembly. The imaging instrument has a view angle other than 0° relative to an optical axis of the imaging instrument, and the imaging instrument is a stereoscopic imaging instrument including first and second image sources. The processing unit is further configured for:

(Continued)

obtaining first image data from the imaging instrument at a first roll position; obtaining subsequent image data from the imaging instrument at a second roll position; and, responsive to a roll movement of the imaging instrument between the first and second roll positions, transitioning between presentation of the first image data on a user display and presentation of the subsequent image data on the user display. The transition includes changing a position of presentation of the first and second image sources.

21 Claims, 32 Drawing Sheets

(51) Int. Cl.
  *A61B 90/00* (2016.01)
  *A61B 1/04* (2006.01)
(52) U.S. Cl.
  CPC ............ *A61B 1/00179* (2013.01); *A61B 1/04* (2013.01); *A61B 34/30* (2016.02); *A61B 90/00* (2016.02); *A61B 2090/364* (2016.02)
(58) Field of Classification Search
  CPC ... A61B 2090/306; A61B 34/00; A61B 34/30; A61B 90/00; A61B 2090/364
  See application file for complete search history.

(56) References Cited

U.S. PATENT DOCUMENTS

| | | | |
|---|---|---|---|
| 5,359,712 A | 10/1994 | Cohen et al. | |
| 5,496,261 A | 3/1996 | Sander | |
| 5,545,120 A | 8/1996 | Chen et al. | |
| 5,547,455 A * | 8/1996 | McKenna | A61B 1/0005 348/65 |
| 5,588,948 A * | 12/1996 | Takahashi | A61B 1/00179 600/111 |
| 5,689,365 A * | 11/1997 | Takahashi | A61B 1/00179 359/362 |
| 5,808,665 A | 9/1998 | Green | |
| 6,191,809 B1 | 2/2001 | Hori et al. | |
| 6,522,906 B1 | 2/2003 | Salisbury, Jr. et al. | |
| 6,799,065 B1 | 9/2004 | Niemeyer | |
| 7,037,258 B2 | 5/2006 | Chatenever et al. | |
| 7,574,250 B2 | 8/2009 | Niemeyer | |
| 8,102,416 B2 * | 1/2012 | Ito | A61B 34/20 348/65 |
| 8,123,675 B2 | 2/2012 | Funda et al. | |
| 9,144,664 B2 * | 9/2015 | Jacobsen | A61B 1/05 |
| 2004/0114146 A1 | 6/2004 | Willis | |
| 2004/0254424 A1 * | 12/2004 | Simkulet | A61B 1/00096 600/176 |
| 2005/0078108 A1 * | 4/2005 | Swift | H04N 7/17318 345/419 |
| 2006/0247521 A1 * | 11/2006 | McGee | A61B 5/0071 600/434 |
| 2007/0167801 A1 * | 7/2007 | Webler | G06T 19/00 600/459 |
| 2007/0197896 A1 * | 8/2007 | Moll | A61B 1/00039 600/407 |
| 2008/0071143 A1 | 3/2008 | Gattani et al. | |
| 2008/0303899 A1 | 12/2008 | Berci | |
| 2009/0059018 A1 * | 3/2009 | Brosnan | G06T 3/4038 348/218.1 |
| 2009/0207241 A1 | 8/2009 | Igarashi et al. | |
| 2010/0125284 A1 | 5/2010 | Tanner et al. | |
| 2010/0296723 A1 * | 11/2010 | Greer | A61B 5/064 382/153 |
| 2011/0071508 A1 * | 3/2011 | Duval | A61B 1/00087 606/1 |
| 2011/0276058 A1 | 11/2011 | Choi et al. | |
| 2011/0277775 A1 * | 11/2011 | Holop | A61B 17/3423 128/849 |
| 2012/0158017 A1 | 6/2012 | Naylor et al. | |
| 2012/0287238 A1 * | 11/2012 | Onishi | A61B 1/0005 348/45 |
| 2012/0289858 A1 * | 11/2012 | Ouyang | A61B 10/0275 600/562 |
| 2013/0038689 A1 | 2/2013 | McDowall | |
| 2013/0046137 A1 * | 2/2013 | Zhao | A61B 1/00181 600/102 |
| 2013/0310648 A1 * | 11/2013 | Kazakevich | A61B 1/00193 600/166 |
| 2014/0148690 A1 * | 5/2014 | Kim | A61B 6/5264 600/424 |
| 2015/0018622 A1 * | 1/2015 | Tesar | A61B 1/05 600/202 |
| 2015/0094571 A1 * | 4/2015 | Bouhnik | A61B 6/037 600/425 |
| 2015/0272694 A1 * | 10/2015 | Charles | A61B 1/32 600/202 |
| 2018/0007322 A1 * | 1/2018 | Kojo | A61B 1/0005 |

FOREIGN PATENT DOCUMENTS

| | | |
|---|---|---|
| CN | 101801254 A | 8/2010 |
| CN | 102438795 A | 5/2012 |
| DE | 19613431 A1 | 10/1996 |
| DE | 102004059143 A1 | 6/2006 |
| DE | 102010041870 A1 | 4/2012 |
| EP | 1925962 A1 | 5/2008 |
| EP | 2424253 A2 | 2/2012 |
| EP | 2441410 A1 | 4/2012 |
| JP | H06269406 A | 9/1994 |
| JP | H10192233 A | 7/1998 |
| JP | 2009297415 A | 12/2009 |
| JP | 2010206495 A | 9/2010 |
| KR | 20090060908 A | 6/2009 |
| WO | WO-9313916 A1 | 7/1993 |
| WO | WO-0135848 A1 | 5/2001 |
| WO | WO-2010093152 A2 | 8/2010 |
| WO | WO-2012001549 A1 | 1/2012 |
| WO | WO-2012003127 A1 | 1/2012 |

OTHER PUBLICATIONS

International Search Report and Written Opinion for Application No. PCT/US15/21110, dated Jun. 8, 2015, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Higuchi T., et al., "Robotic Instrumentation, Personnel and Operating Room Setup," Atlas of Robotic Urologic Surgery, 2011, pp. 15-30.
Warren A., et al., "Horizon Stabilized-Dynamic View Expansion for Robotic Assisted Surgery (HS-DVE)," International Journal of Computer Assisted Radiology and Surgery, Mar. 2012, vol. 7 (2), pp. 281-288.
Moll M., et al., "Unrotating Images in Laparoscopy With an Application for 30° Laparoscopes," IFMBE Proceedings, 2008, vol. 22, pp. 966-969.
Office Action for European Application No. 15764786.8 dated Sep. 17, 2019, 47 pages.

* cited by examiner

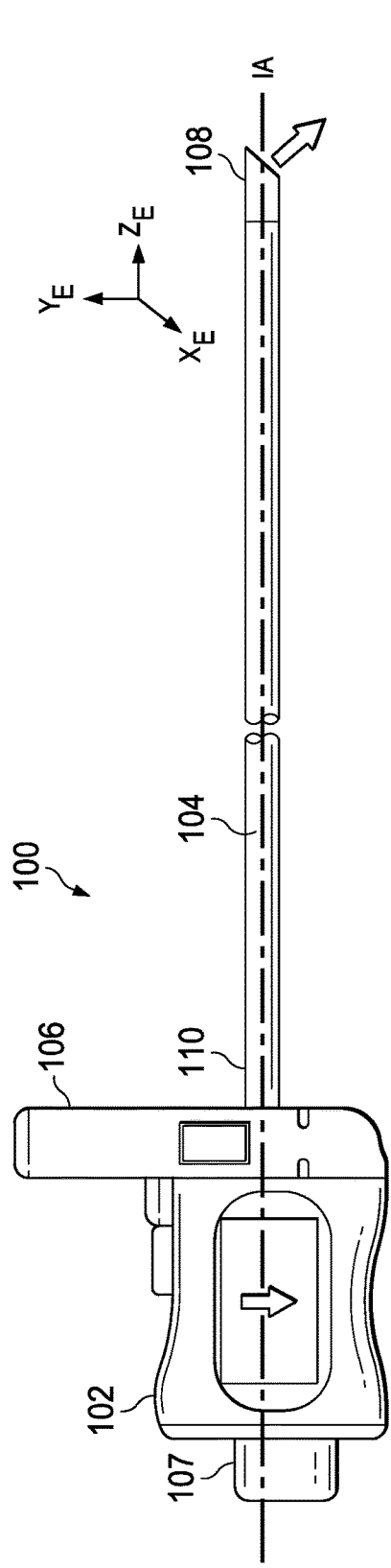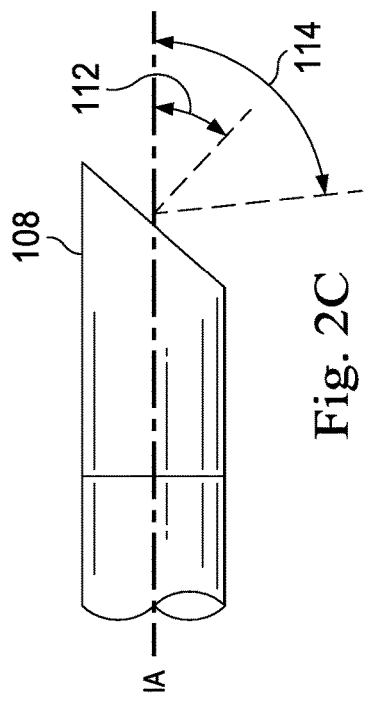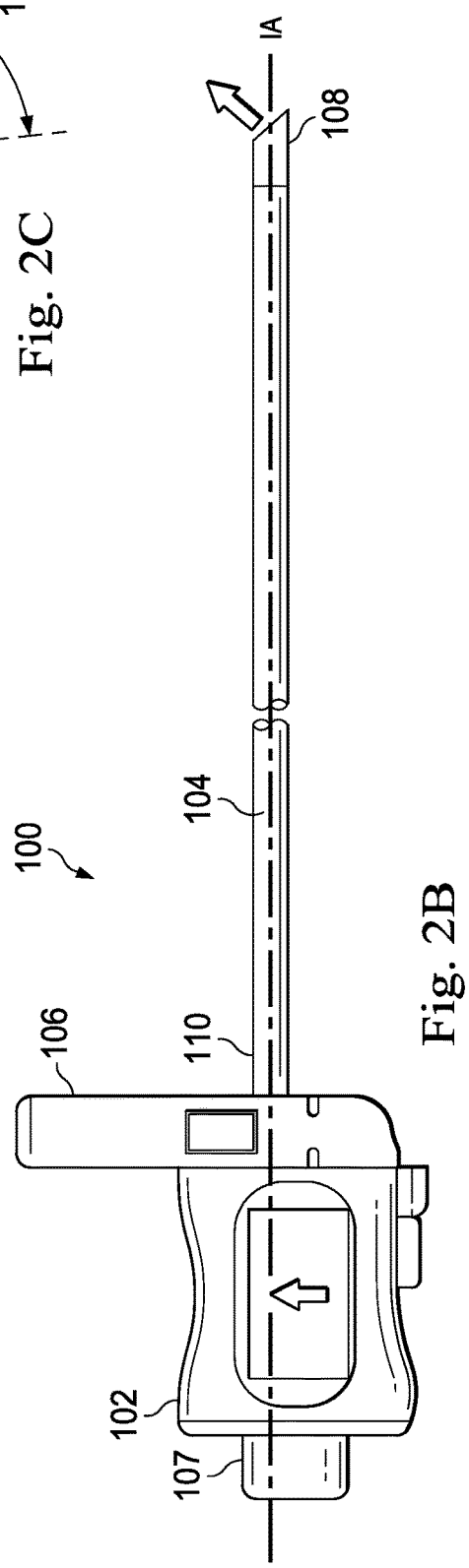

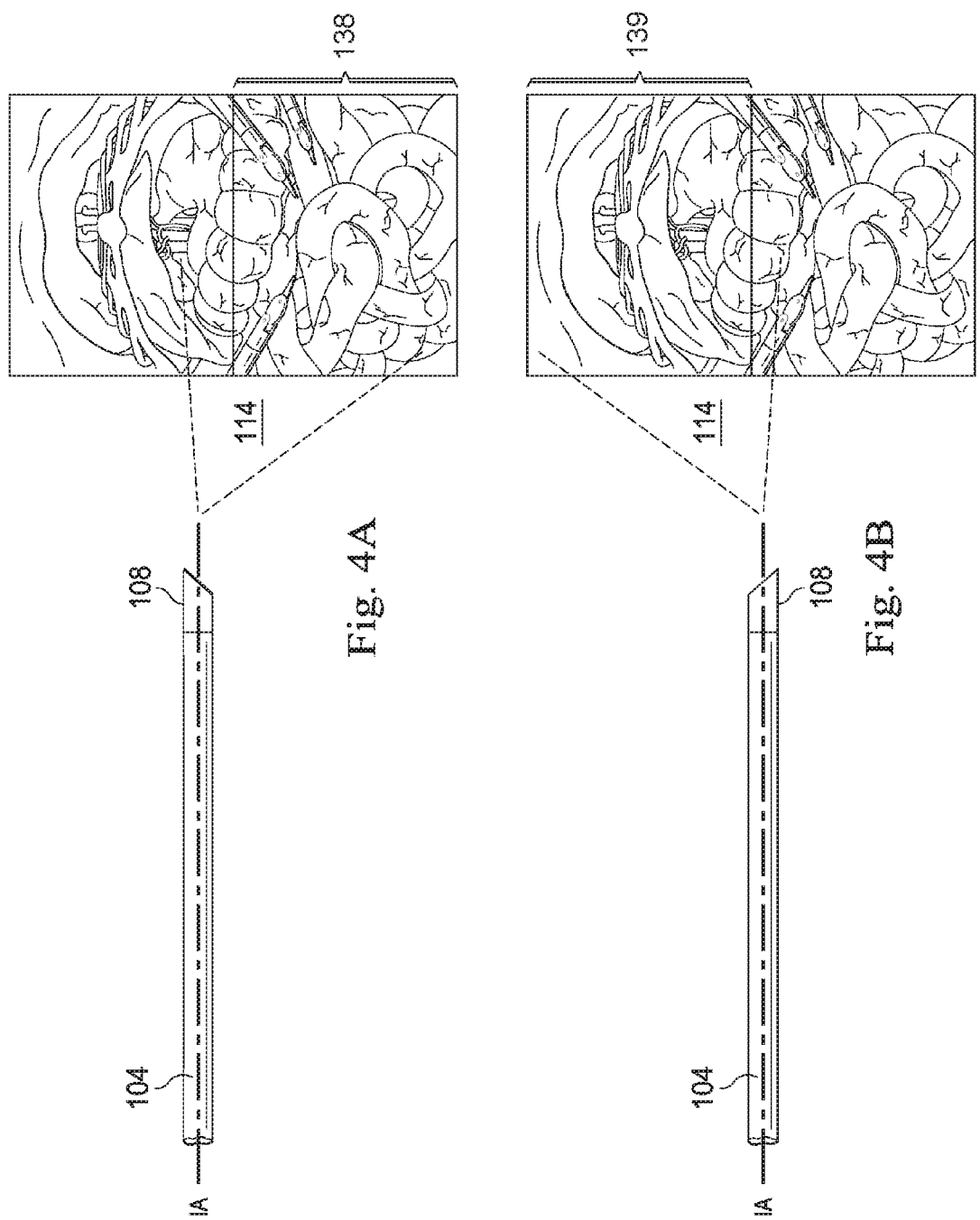

184

186

246

248

SYSTEMS AND METHODS FOR CONTROL OF IMAGING INSTRUMENT ORIENTATION

PRIORITY

This patent application is the U.S. national phase of International Application No. PCT/US2015/021110, filed Mar. 17, 2015, which designated the U.S. and claims priority to and the benefit of the filing date of U.S. Provisional Patent Application 61/954,338, titled "Systems and Methods for Control of Imaging Instrument Orientation," filed Mar. 17, 2014, all of which is are incorporated by reference herein in their entirety.

FIELD

The present disclosure is directed to systems and methods for controlling an imaging instrument and more particularly to systems and methods for remote control of the orientation of an imaging instrument and logical image presentation based upon the orientation.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments include axis view instruments that capture in image of a field of view axially aligned with a central axis of an imaging instrument and off-axis view instruments that capture an image of a field of view angled with respect to the central axis of an imaging instrument. Some minimally invasive medical instruments may be teleoperated or otherwise computer-assisted. Traditionally even with teleoperated procedures, imaging instruments, particularly off-axis view instruments, are manually rotated about the central axis of the instrument to change the orientation of the field of view. Systems and methods are needed to teleoperationally control the orientation of a minimally invasive medical instrument and to logically present the images captured by the rotated instrument to a user.

SUMMARY

Various embodiments of the invention are summarized by the claims that follow below.

In one embodiment, a medical imaging system comprises a teleoperational assembly and a processing unit including one or more processors. The processing unit is configured for receiving a roll position indicator for an imaging instrument coupled to the teleoperational assembly. The imaging instrument has a view angle greater than 0° (e.g., 30°) relative to an optical axis of the imaging instrument. The processing unit is further configured for obtaining first image data from the imaging instrument coupled to the teleoperational assembly at a first roll position and for obtaining subsequent image data from the imaging instrument coupled to the teleoperational assembly at a second roll position. The processing unit is further configured for coordinating a roll movement of the imaging instrument between the first and second roll positions with a transition between presentation of the first image data and the subsequent image data.

In another embodiment, a method of imaging comprises receiving a roll position indicator for an imaging instrument coupled to a teleoperational assembly. The imaging instrument has a view angle greater than 0° (e.g., 30°) relative to an optical axis of the imaging instrument. The method further comprises obtaining first image data from the imaging instrument coupled to the teleoperational assembly at a first roll position and obtaining subsequent image data from the imaging instrument coupled to the teleoperational assembly at a second roll position. The method further comprises coordinating a roll movement of the imaging instrument between the first and second roll positions with a transition between presentation of the first image data and the subsequent image data.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 2A illustrates an off-axis endoscopic imaging instrument in first orientation.

FIG. 2B illustrates the off-axis endoscopic imaging instrument of FIG. 2A in a second orientation.

FIG. 2C illustrates the distal end of the off-axis endoscopic imaging instrument of FIG. 2A.

FIG. 4A illustrates the off-axis endoscopic imaging instrument of FIG. 2A in the first orientation with a first field of view of a patient anatomy.

FIG. 4B illustrates the off-axis endoscopic imaging instrument of FIG. 2A in the second orientation with a second field of view of the patient anatomy.

DETAILED DESCRIPTION

Figure 1A:
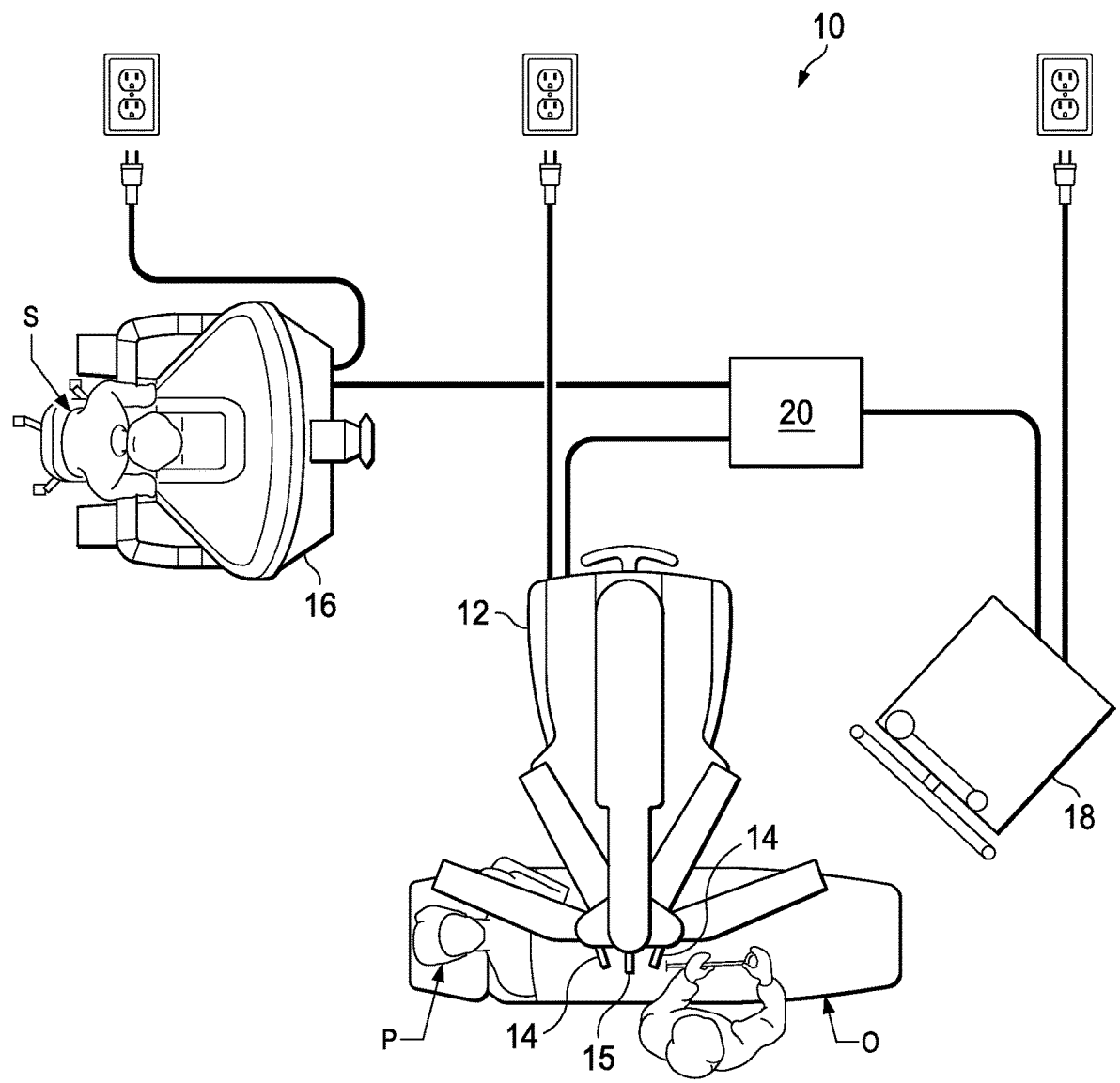
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a teleoperational medical system for use in, for example, medical procedures including diagnostic, therapeutic, or surgical procedures, is generally indicated by the reference numeral 10. A teleoperational medical system may be, for example, a robotic surgical system. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 12 supports and manipulates the medical instrument system 14 while the surgeon S views the surgical site through the console 16. An image of the surgical site can be obtained by the endoscopic imaging system 15, such as a stereoscopic endoscope, which can be manipulated by the teleoperational assembly 12 to orient the endoscope 15. An electronics cart 18 can be used to process the images of the surgical site for subsequent display to the surgeon S through the surgeon's console 16. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 10 also includes a control system 20. The control system 20 includes at least one memory and at least one processor (not shown), and typically a plurality of processors, in a processing unit for effecting control between the medical instrument system 14, the operator input system 16, and an electronics system 18. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The teleoperational medical system 10 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 1B:
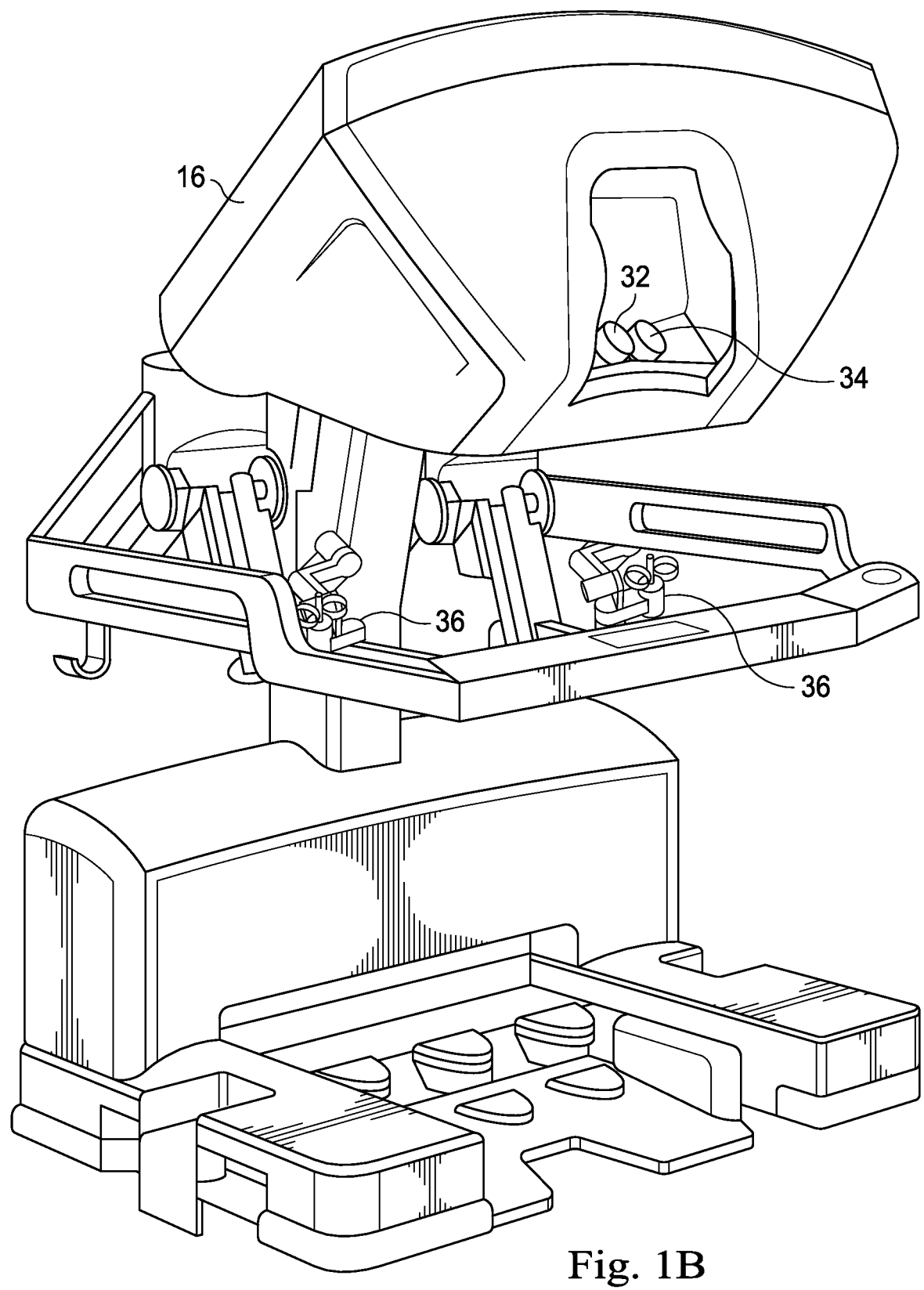
FIG. 1B is a perspective view of a surgeon's control console for a teleoperational medical system, in accordance with many embodiments.

FIG. 1B is a perspective view of the surgeon's console 16. The surgeon's console 16 includes a left eye display 32 and a right eye display 34 for presenting the surgeon S with a coordinated stereo view of the surgical site that enables depth perception. The console 16 further includes one or more input control devices 36, which in turn cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36.

Figure 1C:
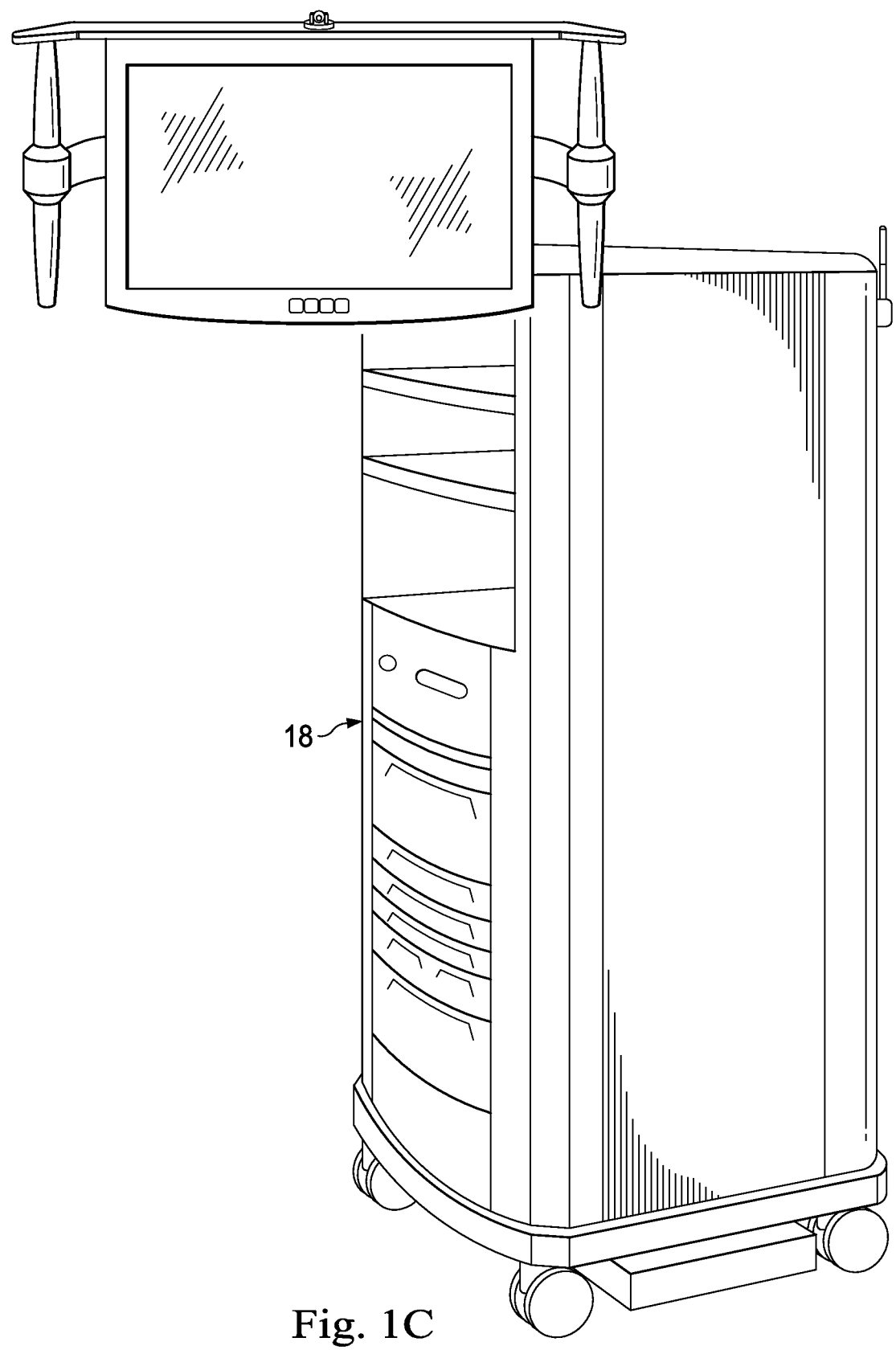
FIG. 1C is a perspective view of a teleoperational medical system electronics cart, in accordance with many embodiments.

FIG. 1C is a perspective view of the electronics cart 18. The electronics cart 18 can be coupled with the endoscope 15 and can include a processor to process captured images for subsequent display, such as to a surgeon on the surgeon's console, or on another suitable display located locally and/or remotely. For example, where a stereoscopic endoscope is used, the electronics cart 18 can process the captured images to present the surgeon with coordinated stereo images of the surgical site. Such coordination can include alignment between the opposing images. As another example, image processing can include the use of previously determined camera calibration parameters to compensate for imaging errors of the image capture device, such as optical distortions. The electronics cart 18 may also include a display monitor and components of the control system 20.

Figure 1D:
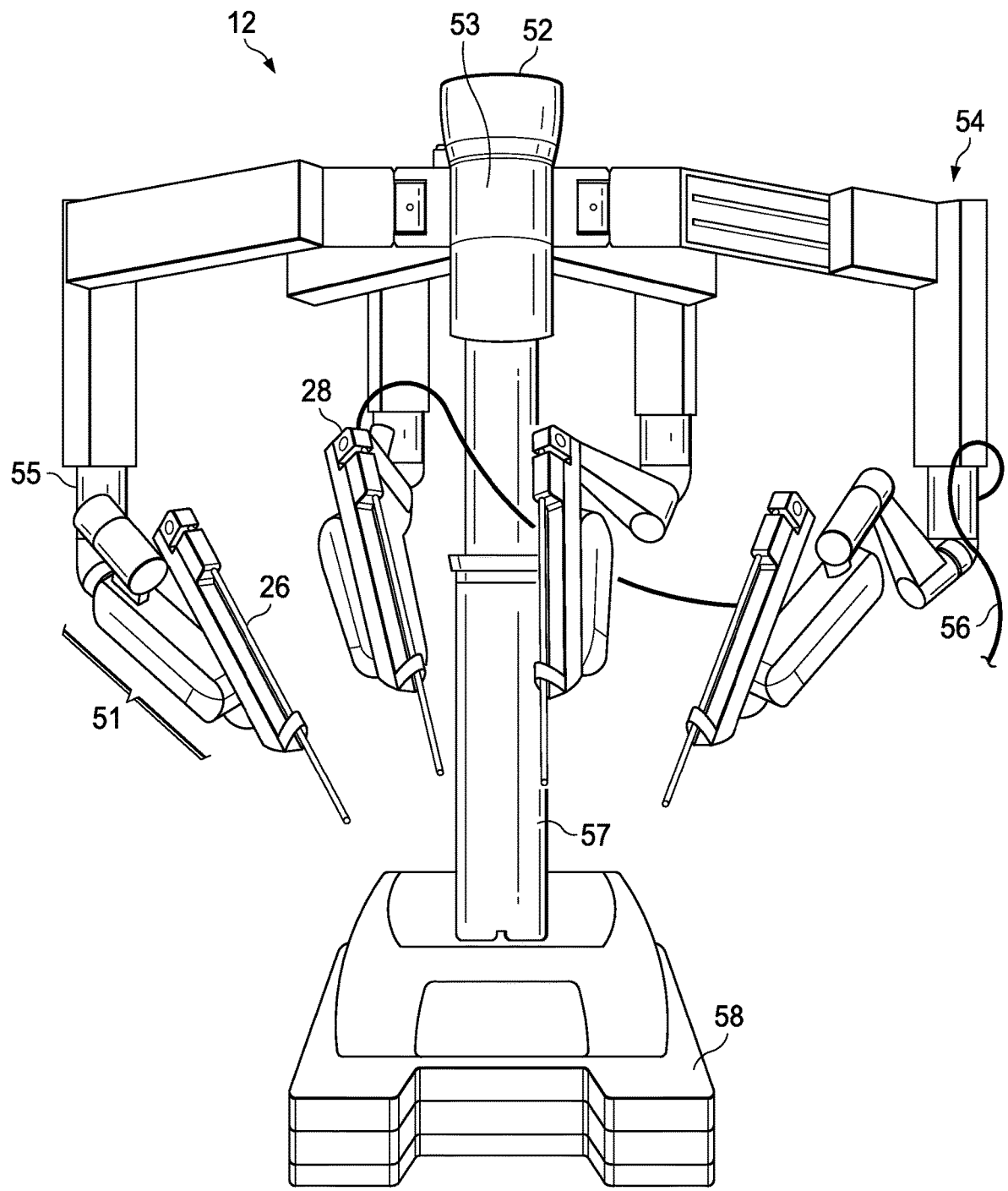
FIG. 1D is a perspective view of a patient side cart, according to one example of principles described herein.

FIG. 1D is a perspective view of one embodiment of a teleoperational assembly 12 which may be referred to as a patient side cart. The patient side cart 12 shown provides for the manipulation of three surgical tools 26 (e.g., instrument systems 14) and an imaging device 28 (e.g., endoscopic imaging system 15), such as a stereoscopic endoscope used for the capture of images of the site of the procedure. The imaging device may transmit signals over a cable 56 to the electronics cart 18. Manipulation is provided by teleoperative mechanisms having a number of joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

The patient side cart 12 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 12 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument 26. The manipulator arms 51 may be teleoperatable. In some examples, the arms 54 connecting to the orienting platform are not teleoperatable. Rather, such arms 54 are positioned as desired before the surgeon S begins operation with the teleoperative components.

Endoscopic imaging systems (e.g., systems 15, 28) may be provided in a variety of configurations including rigid or flexible endoscopes. Rigid endoscopes include a rigid tube housing a relay lens system for transmitting an image from a distal end to a proximal end of the endoscope, where it is then typically captured by an image sensor (or sensors, in the case of a stereo endoscope). Current rigid endoscopes may also package the optics and cameras inside the shaft of the endoscope itself, making a more compact, lightweight, and generally higher-performing image acquisition system.

Another class of endoscopes, flexible endoscopes, transmits images inside one or more flexible optical glass fibers to a proximal camera or cameras. Current flexible endoscopes can also be constructed with a small camera module located directly at the distal end of the scope, near the surgical site. This camera is located in a small housing, attached to the endoscope shaft with flexible joint (or joints) which can then be maneuvered via control linkages (e.g., steel cables) in order to dynamically change the viewing direction relative to the main axis of the endoscope shaft.

In order to provide the ability to view more of the interior of the human body, rigid endoscopes may be provided with different tip viewing angles, including a 0° viewing angle for forward axial viewing or units with fixed viewing angles between 0° and 90° for oblique viewing. A 30° viewing angle, as measured from the main longitudinal axis of the endoscope shaft, is very common for medical endoscopy. This creates an endoscope with a tip that looks like a "chisel-tip" or "wedge-shaped tip."

Digital-image based endoscopes have a "chip on tip" (COT) design in which a distal digital sensor such as a one or more charge-coupled device (CCD) or a complementary metal oxide semiconductor (CMOS) devices acquire the image data. These imaging chips are used with small lens assemblies which are mounted inside the endoscope shaft, distal of the imager(s).

Endoscopic imaging systems may provide two- or three-dimensional images to the viewer. Two-dimensional (2D) images may include a single camera and provide limited depth perception. Three-dimensional (3D) stereo endoscopic images may provide the viewer with more accurate depth perception. Stereo endoscopic instruments typically employ two cameras, physically spaced a small distance apart, to capture stereo images of the patient anatomy. The two images, taken from two slightly different locations, contain optical parallax information. This parallax information, when displayed in a properly-designed stereo viewer, present the viewer with a slightly different view of the surgical site into each eye, which re-creates the three-dimensionality of the surgical site being viewed by the two cameras.

FIG. 2A illustrates a rigid off-axis stereo endoscopic imaging instrument 100 including a handle 102 and a shaft 104 rigidly coupled to the handle. A roll adaptor 106 is rotatably coupled to the shaft 104 and/or the handle 102. The shaft includes a distal end 108 and a proximal end 110. Distal end 108 houses a distal imaging device, lens systems, optical fibers, or other stereo image capture and transmission components (not shown). The distal end 108 may include a stereo pair of image sensors mounted behind optic elements and a sealed sapphire window. Alternatively, handle 102 contains the imaging devices and the image is relayed up shaft 104 optically via a system of lenses or optical fiber(s). The shaft 104 extends along an insertion axis IA. A cable 107 extends from the handle and is an interface between electronics cart 18 and endoscope 100. The cable 107 may contain illumination light fiber bundle(s) and communication lines from electronics cart 18 to the handle 102. As shown in FIG. 2C, the instrument 100 has an angle of view 112 and an optical field of view shown in cross-section as 114. In this embodiment, the angle of view is approximately 30° but may be any angle suitable for oblique angle viewing with respect to the insertion axis IA. Responsive to manual or teleoperational control, the teleoperational assembly (e.g., assembly 12) may be operated to rotate the imaging instrument 100, including the instrument body 102 and the shaft 104, about the insertion axis IA. FIG. 2A illustrates the imaging instrument 100 with a −30° or downward angle with respect to the insertion axis IA. Roll adapter 106 stays in a constant orientation and position. FIG. 2B illustrates the imaging instrument 100 rotated 180° with a +30° or upward angle with respect to the insertion axis IA. Roll adapter 106 stays in a constant orientation and position. The optical transmission system within the shaft 104 and distal digital sensor(s) may be packaged in a variety of ways known in the art. When the imaging instrument 100 is rotated about the insertion axis IA, the optical components in the shaft 104 and the distal digital sensor(s) rotate together with the shaft. The terms "up", "down", "upward, and "downward" are used for illustrative purposes only to label generally opposite directions and are not intended to be limiting.

Figure 2D:
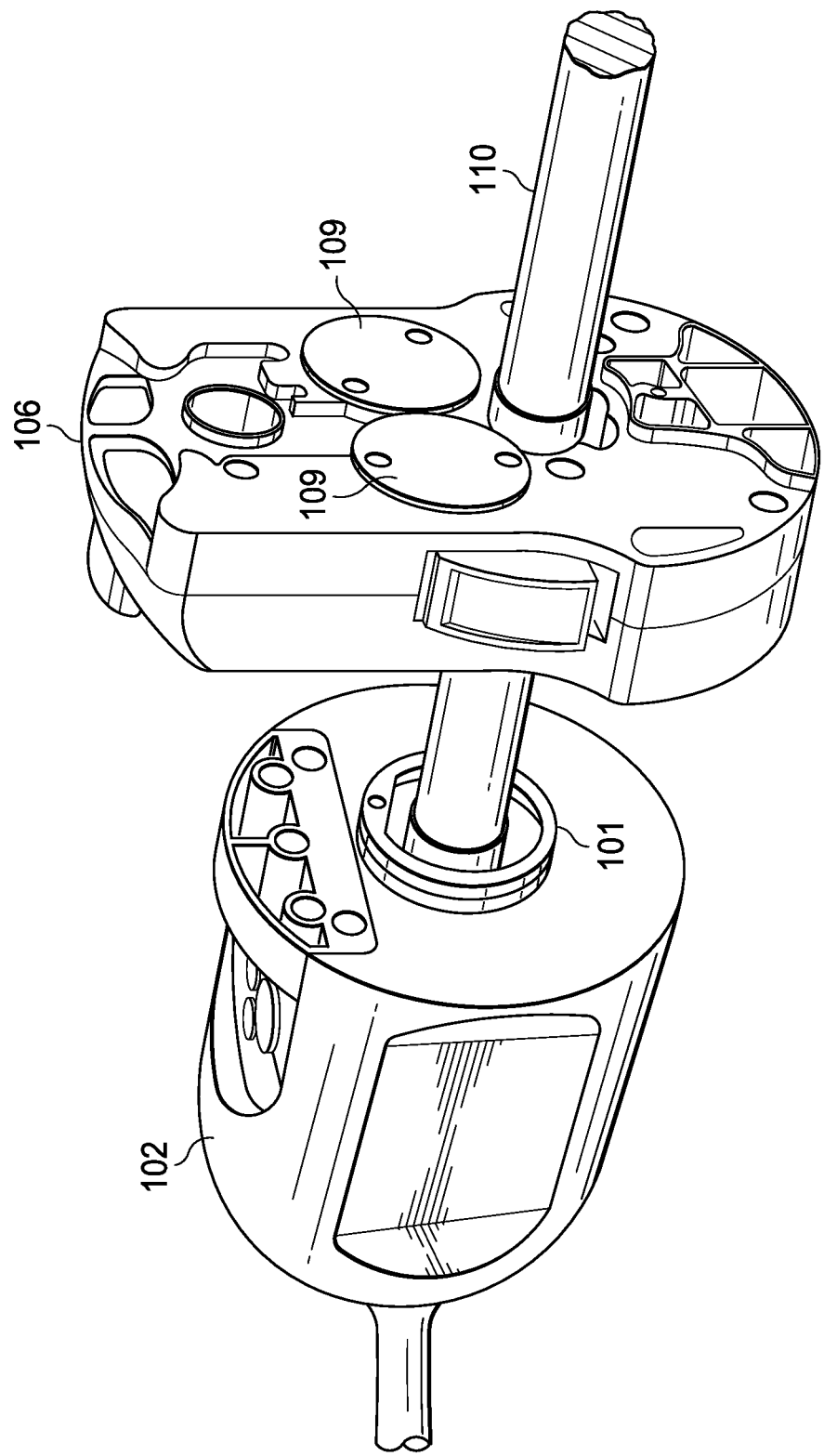
FIG. 2D illustrates the coupling of the handle and adaptor for the off-axis endoscopic imaging instrument of FIG. 2D.
Figure 2E:
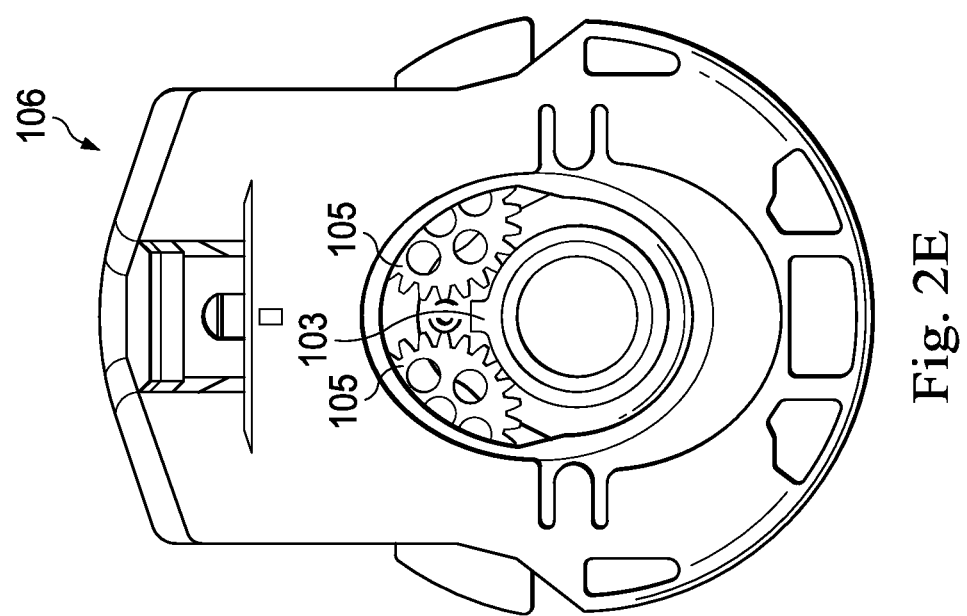
FIG. 2E illustrates the adaptor in greater detail.

FIG. 2D illustrates the coupling of the instrument handle 102 and the roll adaptor 106. The adaptor 106 provides an interface for mounting the endoscope to the manipulator of the teleoperational system as well as a mechanism for controlling roll of the endoscope while attached to the arm. The handle 102 includes a keyed collar 101 to which the roll adaptor 106 is coupled. The keyed collar 101 allows rotation of the adaptor 106 with respect to the handle 102. As shown in FIG. 2E, the adaptor 106 provides a gear transmission 105 between discs 109 used by the manipulator arm and provides a keyed roller 103 which couples with the keyed collar 101. The endoscope handle has a magnetic sensor which can detect the polarity of two permanent magnets mounted in the adaptor 106. This enables the endoscope to sense two discrete roll positions of the adaptor near 0° and 180° alignment. The 30° down configuration corresponds to the adaptor 106 at its 0° roll position. The 30° up configuration corresponds to the adaptor at its 180° roll position. The discs 109 of the adaptor 106 couple to an instrument sterile adaptor which couples to an instrument carriage on the manipulator arm 51. The instrument carriage includes a set of independent motors (e.g., 2 or more motors) that drive corresponding disks in the instrument sterile adaptor. The disks 109 of the roll adaptor 106 couple with two roll disks of the instrument sterile adaptor to rigidly constrain the adaptor 106 in position and orientation. The roll disks of the sterile adaptor mated with the disks 109 of the adaptor allow the teleoperational system to sense and control the roll angle of the endoscope.

Figure 2F:
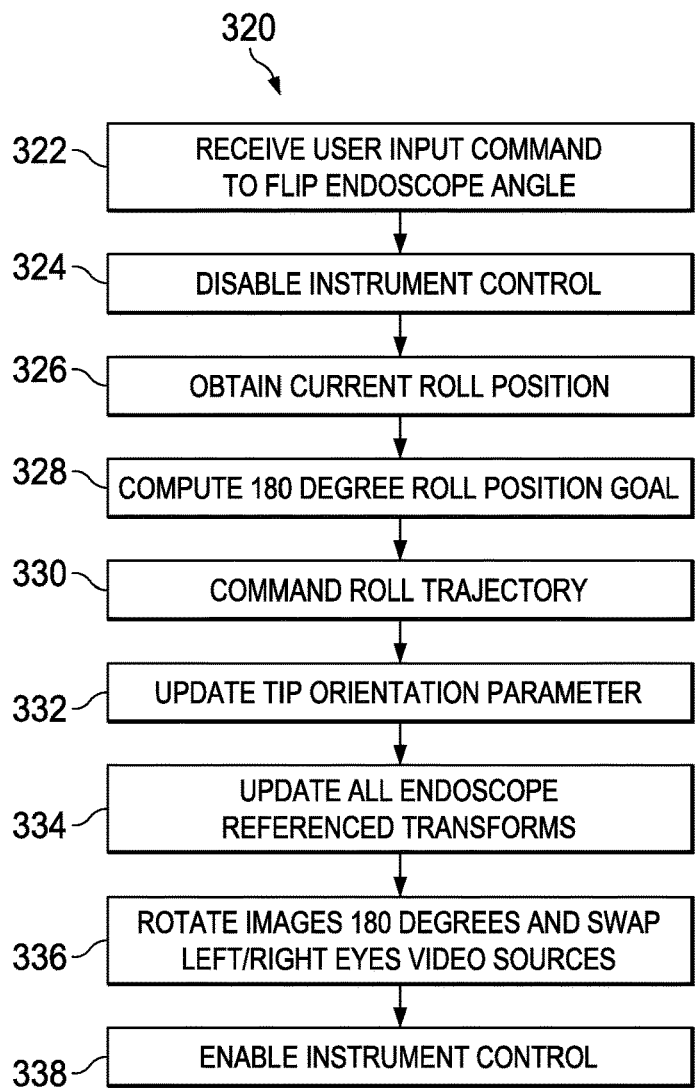
FIG. 2F illustrates a method for transitioning between scope angle settings.
Figure 2G:
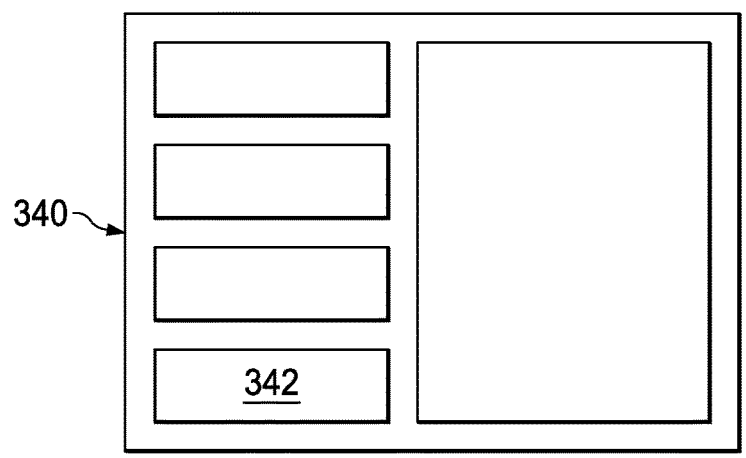
FIG. 2G illustrates a user input touchpad.

FIG. 2F illustrates a method 320 for transitioning between endoscope angle settings. At a process 322, a user input command is received to flip the endoscope angle (e.g. 30° up to 30° down or vice versa). The user selection may be provided via a console touchpad 340 as shown in FIG. 2G. The console touchpad 340 may be a component of the operator input system 16. The console touchpad 340 includes a touch screen button 342 which transmits the user's selection to the control system 20. In alternative embodiments, the user input may be provided via detected user motion, a switch on the control devices 36, a dedicated switch on the operator input system 16, a switch anywhere within the teleoperational system 10 operated by a user body part, a verbal command, an eye gaze command, or a user controlled implement (e.g., a mouse).

At a process 324, the control system 20 temporarily disables the surgical instrument control because the instruments tips may be outside of the endoscope's field of view after the transition. At a process 326, the current roll position is obtained.

At a process 328, a 180° roll orientation goal is computed. idea as if the user is tilting his head, i.e., transitioning from looking down at his feet to looking up at the sky. With an angled endoscope, a transition between, for example, 30° down to 30° up (or vice versa), is accomplished by rolling the endoscope about axis IA by 180 degrees from the current orientation to the new orientation.

The endoscope and carriage degrees of freedom are capable of infinite roll motion. This means that the scope can be rolled to any new angular position from any current angular position in either the clockwise or counter-clockwise direction. However, generally, continuous winding of the endoscope cable should be avoided. Therefore, the control system may impose a software-based limit on the roll range of motion to prevent the endoscope from rolling more than one revolution in either direction. The direction for roll motion when performing a scope angle change will roll in the direction away from the closest roll limit. This minimizes the twist induced in the cable attached to the endoscope.

At a process 330, a roll trajectory is commanded to produce a smooth and continuous motion of roll position and velocity. For example, if commanded from the console touchpad 340, the roll may be performed quickly (e.g., in less than 0.5 seconds) so that the transition is complete when the user's head returns to the viewer. At a process 332, a tip orientation parameter is updated. The kinematic parameter that controls the orientation of the endoscope tip frame of reference is adjusted to incorporate the new roll position. This may be achieved by applying a 180° rotation offset about the local z-axis of the tip frame of reference.

At a process 334, all endoscope referenced transforms are updated. All instrument arms map their motions into the endoscope tip coordinate space. This update is performed before re-enabling instrument control. At a process 336, images are rotated 180° and the left and right eye video sources are swapped. The stereoscopic imagery displayed on the display system is thus transformed to account for the physical roll of the endoscope, otherwise everything would appear up-side down. This transformation is achieved by rotating the individual image frame buffers by 180°. In addition, the left and right eye image sources are swapped. At a process 338, the instrument control is re-enabled after the roll transition is complete.

As mentioned, the endoscope handle also includes a sensor for discrete sensing of two configurations—the 0° and 180° positions (e.g., corresponding to the 30° up and 30° down positions of a 30° angled endoscope. This feature is used when the scope is being hand-held by the surgeon or operating room assistant. When coupled to the teleoperational surgical manipulator, this sensor is disabled because the roll position of the endoscope may be determined directly by the angle of the roll adaptor carriage drive disks, once the endoscope has been installed and engaged correctly on teleoperational arm instrument carriage.

Figure 3:
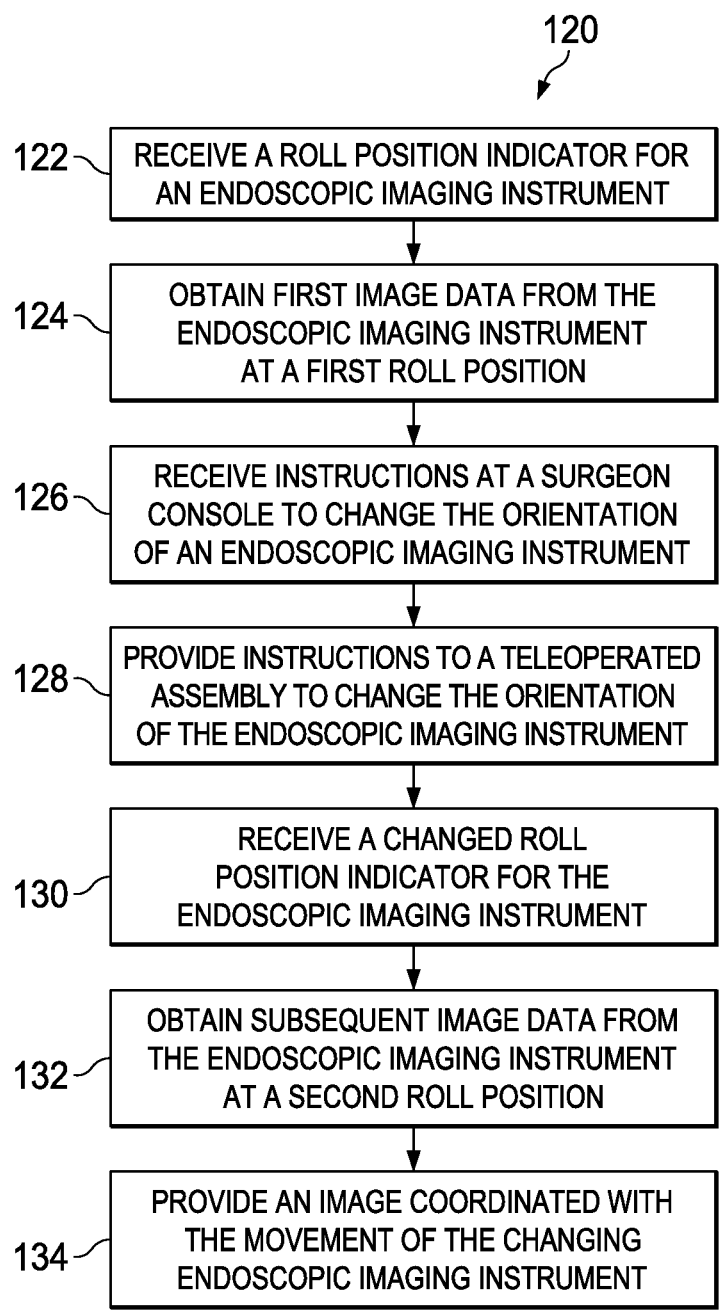
FIG. 3 illustrates a method for changing the roll position of an endoscopic imaging instrument.

FIG. 3 illustrates a method for changing the roll position of an endoscopic imaging instrument 100. The method provides for coordination of the instrument roll operation with the presentation of images selected to minimize viewer disorientation. The method includes a process 122 for receiving a roll position indicator (i.e., an indication of which roll position the endoscopic instrument is currently in) from the roll sensor(s). In alternative embodiments, the roll position indicator may be provided by the instrument 100 itself or from other types of sensor systems configured to recognize the roll position of the instrument. The roll position indicator may indicate, for example, that the 30° degree viewing angle of the instrument 100 is directed in an upward position or in a downward position that is 180° rotated from the upward position. The method 120 includes a process 124 for obtaining first image data from the instrument 100 at a first roll position (e.g., 30° upward) indicated by the position indicator. The method includes a process 126 of receiving input from a surgeon console (e.g., console 16) to change the roll angle of the instrument 100 so as to position the instrument in a second roll position. The input may be received from an input control device (e.g., device 36) or another actuator (or input device such as a small touch screen part of the surgeon console) located at the surgeon console. The instructions for changing the roll angle are received by a control system (e.g., control system 20). In a process 128, the control system provides a signal through the manipulator arm (e.g., arm 51) to which the instrument is attached to activate motors to rotate the instrument 100 to the desired roll angle. The instrument is thus positioned in the second roll position. In a process 130, a changed roll position indicator is received from the adaptor 106 or other roll sensors. In a process 132, subsequent image data is obtained from the instrument 100 positioned in the second roll position. If, for example, the image data is continuously received video data, subsequent image data may be data for a frame of video immediately following the first image data or may be data for a frame of video that is two or several more frames after the first image data frame of video.

In a process 134, an image, coordinated with the movement of the rotating instrument, is provided on a display. As the instrument is rotated between the initial angular position and the selected angular position, the images presented to the viewer may be chosen to logically depict the changing view of the patient anatomy and to minimize disorientation for the viewer. The generated images may include a rotated image from either the first or subsequent image data based upon the roll position indicator. In other words, the roll position indicator may indicate that one or more of the images captured by the instrument 100 should be rotated to minimize viewer disorientation, as will be described in greater detail below. This process also involves compensating kinematic parameters to account for the physical roll of the endoscope and to preserve upright orientation of the endoscope tip. When the endoscope is rotated from the 30° up to the 30° down configuration, the tip frame of reference is effectively rotated about the $X_S$ axis by 60°. To achieve this view change in actuality, the endoscope is physically rolled 180° from its current roll position and a 180° roll offset is applied along the ZS axis of the endoscope tip frame of reference. This roll offset corrects the system and viewer's sense of being right-side-up or upside-down. When the system rolls the endoscope by 180°, it also determines which direction to rotate. The direction is chosen to remain within the software roll limitations of the endoscope. Although the endoscope and manipulator carriage degrees of freedom can support infinite roll, roll limitations may be imposed to prevent endoscope cable wind-up.

FIG. 4A illustrates the distal end 108 of the shaft 104 of the off-axis endoscopic imaging instrument 100 of FIG. 2A in an initial orientation with the field of view 114 directed on an initial area 138 of a patient P's anatomy. FIG. 4B illustrates the distal end 108 of the shaft 104 of the off-axis endoscopic imaging instrument 100 in a final orientation with the field of view 114 directed on an final area 139 of a patient P's anatomy.

Figure 5A:
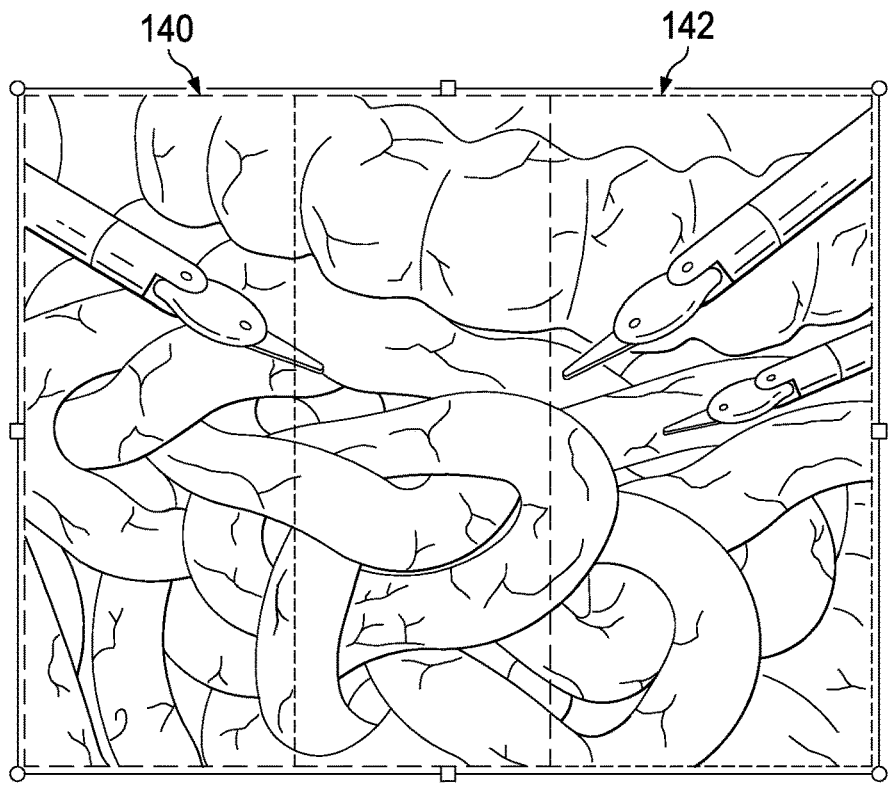
FIG. 5A illustrates a stereoscopic pair of images from the first field of view with the endoscopic imaging instrument in the first orientation.
Figure 5B:
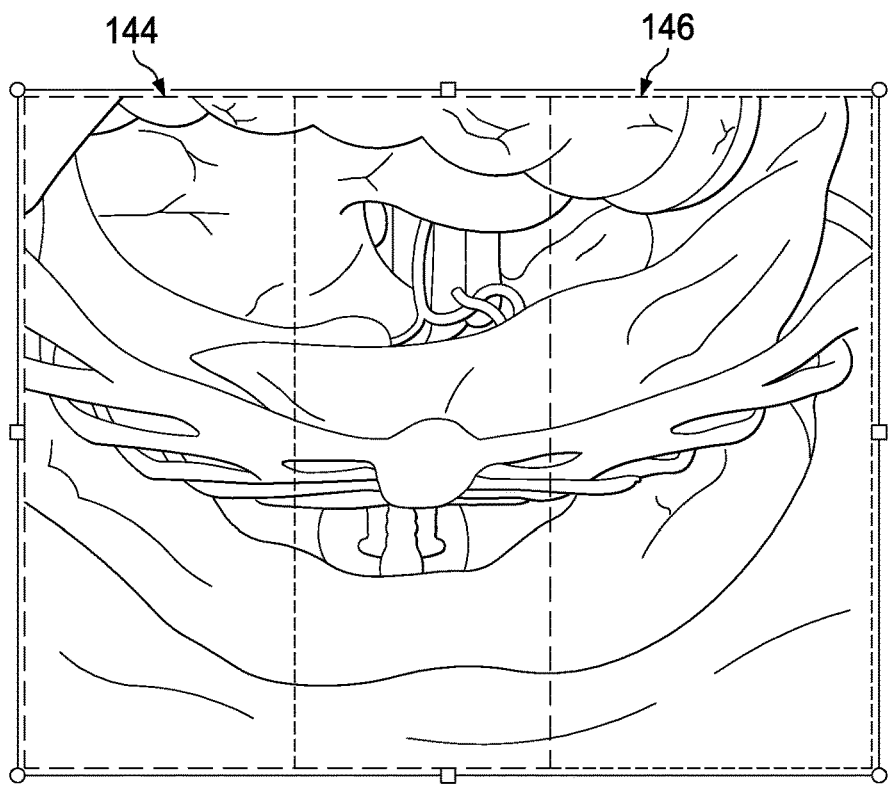
FIG. 5B illustrates a stereoscopic pair of images from the second field of view with the endoscopic imaging instrument in the second orientation.
Figure 5C:
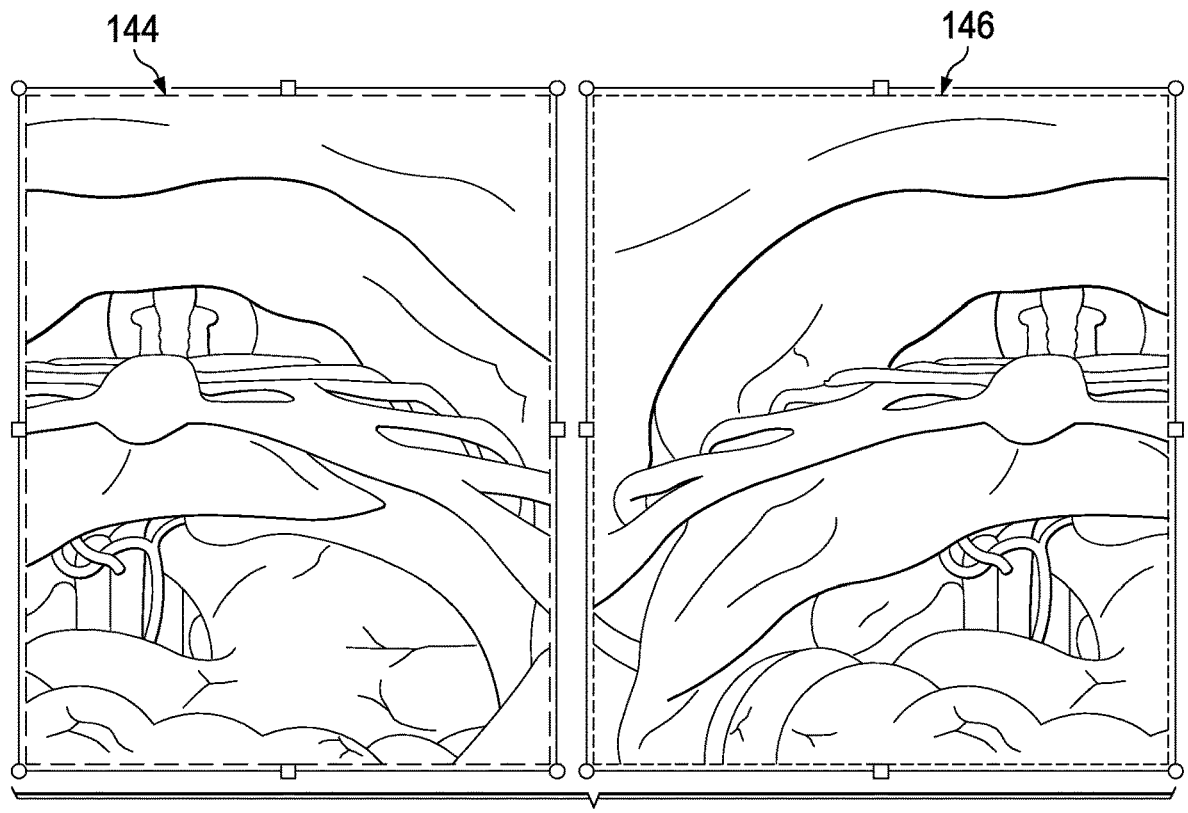
FIG. 5C illustrates each of the images of the stereoscopic pair of images rotated at the same angle of rotation as the second orientation of the off-axis endoscopic imaging instrument.
Figure 5D:
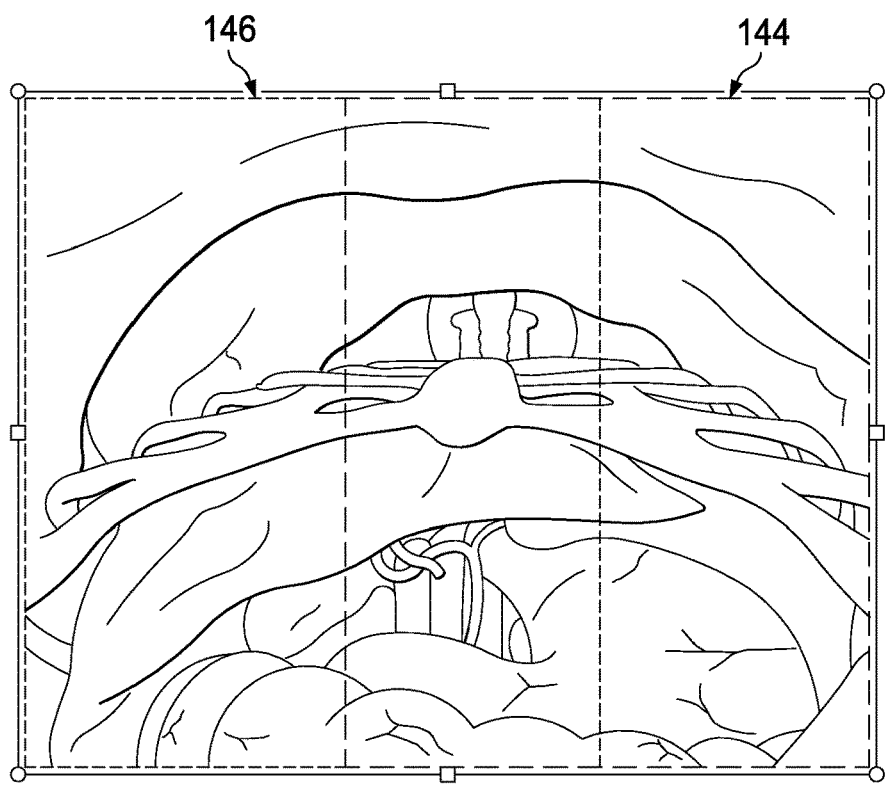
FIG. 5D illustrates each of the images of the stereoscopic pair of images in swapped positions as compared to FIG. 5C.

FIG. 5A illustrates a stereoscopic pair of images 140, 142 with the field of view 114 of the instrument 100 directed at the initial area 138 of the patient P's anatomy as in FIG. 4A. The images 140, 142 overlap to produce a stereoscopic image (amount of overlap shown is small in order to more clearly illustrate the embodiment). FIG. 5B illustrates a stereoscopic pair of overlapping images 144, 146 with the field of view 114 of the instrument 100 rotated 180° and directed at the final area 139 of the patient P's anatomy as in FIG. 4B. The paired images 144, 146 appear to be upside down and thus may be disorienting to a viewer and limit the viewer's ability to effectively perform an interventional procedure in the area 139. To preserve the user's sense of orientation as well as proper stereoscopic disparity, the images 144, 146 may be rotated 180° and swapped when presented to the left and right eyes of the viewer. For example, as shown in FIG. 5C, the left and right eye video sources depicted by images 144 and 146 respectively may be rotated 180°. Additionally as shown in FIG. 5D, the left and right eye video sources may be swapped to preserve the stereoscopic mapping to the user's left and right eyes. To minimize viewer disorientation, the image changes between FIG. 5A and FIG. 5D may be coordinated in a variety of different ways to preserve the continuity of imagery and spatial orientation. Thus, following a user request to look "up," the system can accomplish this simply by rolling the instrument 180°, swapping the images to the left and right eyes, and rotating the images by 180°.

Figure 6:
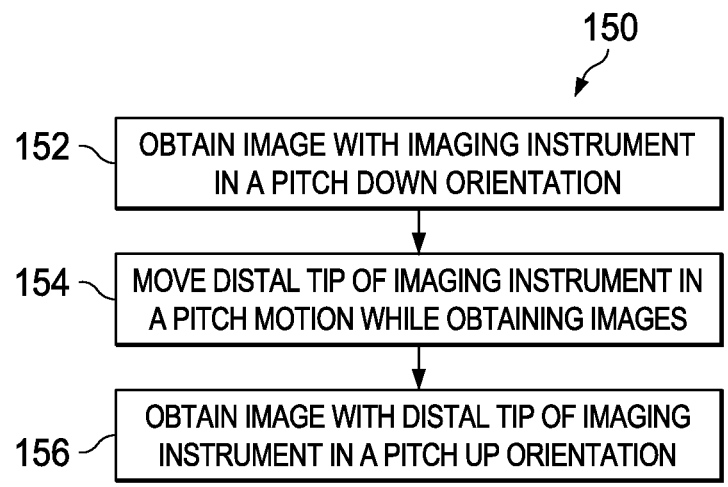
FIG. 6 illustrates a method for changing the presentation of the images gathered while changing the orientation of an endoscopic imaging instrument, according to one embodiment of the present disclosure.
Figure 7A:
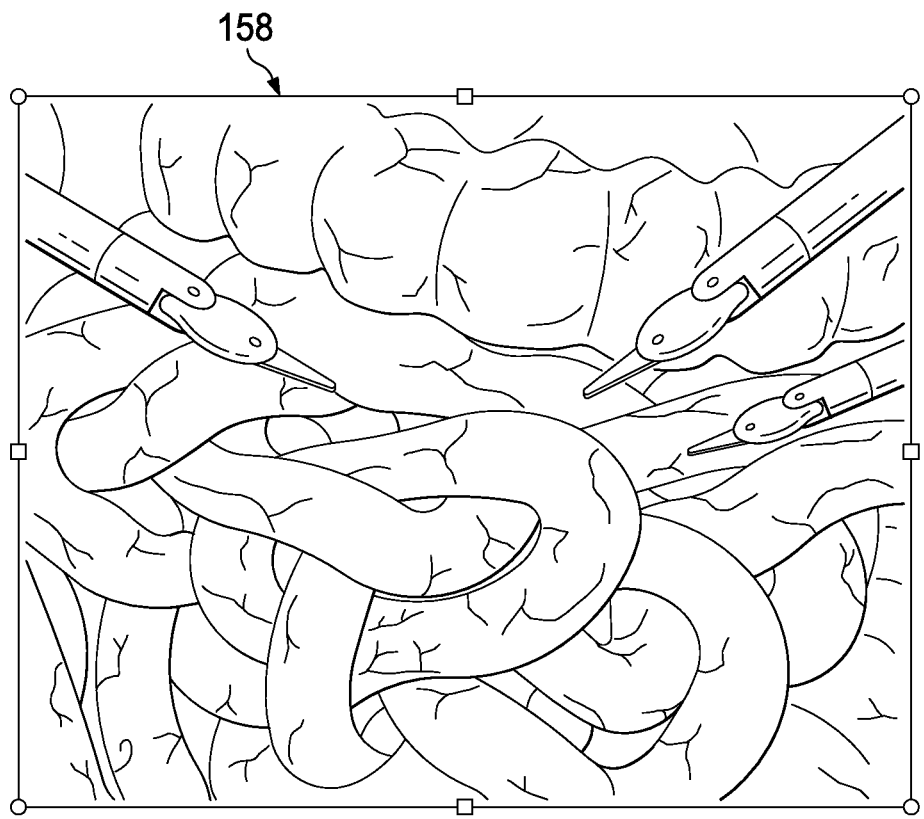
FIG. 7A-7C illustrates a series of presented images associated with the method of FIG. 6.
Figure 7B:
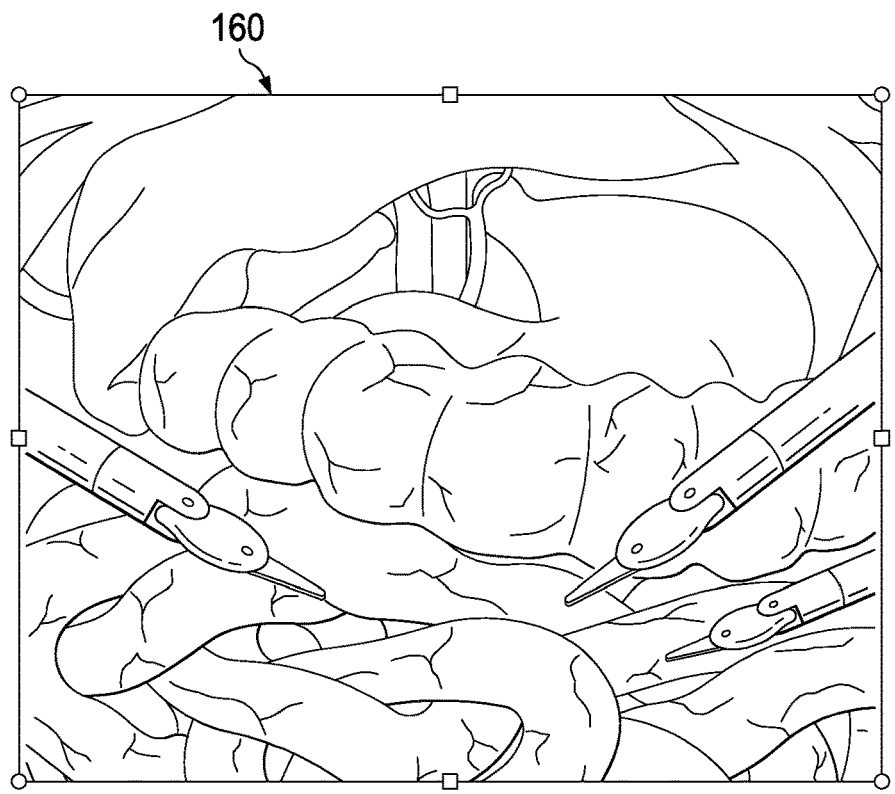
Figure 7C:
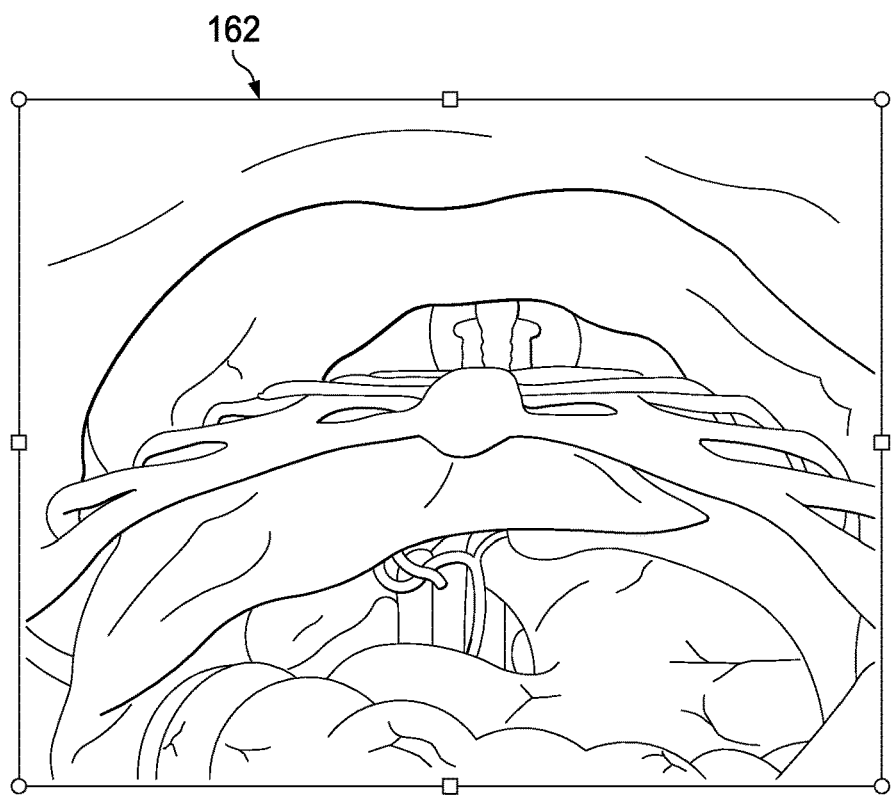

FIGS. 6 and 7A-7C illustrate one method for presenting images captured while changing the direction of the field of view of an endoscopic instrument according to one embodiment of the present disclosure. This implementation provides a continuous transition from a downward field of view to an upward field of view, while preserving continuity of imagery and spatial orientation. Rather than using a fixed 30° viewing angle endoscopic instrument, this implementation may be achieved using an endoscopic instrument without axial rotation if the endoscopic instrument has a distal end capable of a rotational pitch motion (e.g., a flexible endoscope as opposed to a "fixed-angle" endoscope). As shown in FIG. 6, a process 152 includes obtaining a stereoscopic image, such as image 158 (FIG. 7A) of a patient anatomy, with a distal end of an endoscopic imaging instrument in a pitch down 30° orientation (with respect to the axis of the instrument shaft). A process 154 includes moving the distal end of the endoscopic imaging instrument in a pitch up motion while capturing images of the patient anatomy. During the pitch up motion, an image 160 is captured at approximately 0° orientation (with respect to the axis of the instrument shaft). A process 156 includes obtaining a stereoscopic image, such as image 162 (FIG. 7C) of the patient anatomy, with the distal end of the endoscopic imaging instrument in a pitch up 30° orientation (with respect to the axis of the instrument shaft). The method 150, using a pivoting distal end instrument, provides on example of an idealized continuous transition between a downward and upward field of view. Image presentation implementations that employ a rigid off-axis endoscopic instrument (e.g., instrument 100) rotating about the instrument's insertion axis may be coordinated to approximate the example transition shown in images 158-162.

Figure 8:
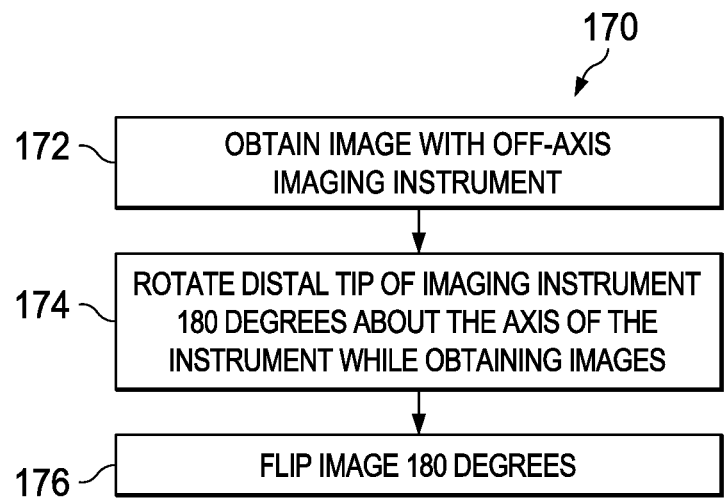
FIG. 8 illustrates a method for presenting images captured while changing the orientation of an endoscopic imaging instrument, according to another embodiment of the present disclosure.
Figure 9A:
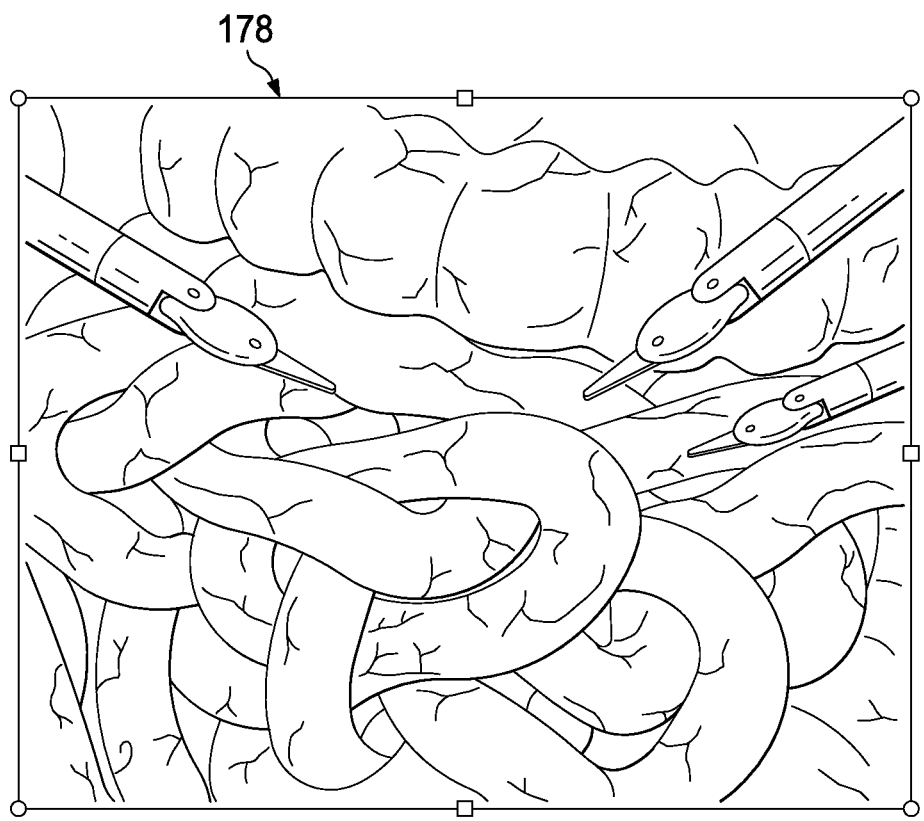
FIG. 9A-9E illustrates a series of presented images associated with the method of FIG. 8.
Figure 9B:
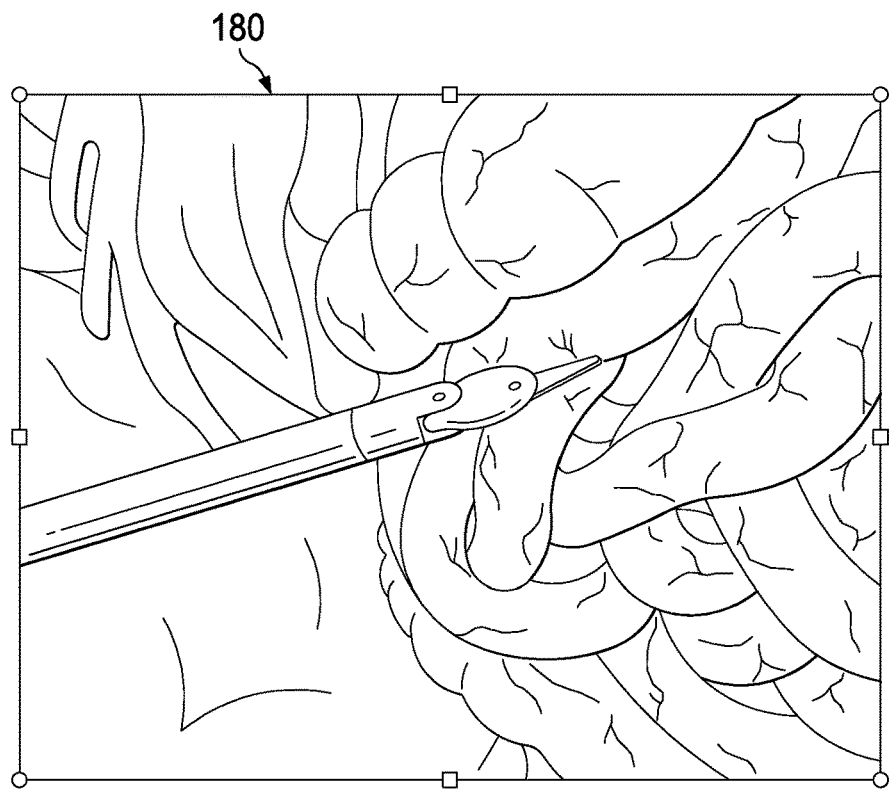
Figure 9C:
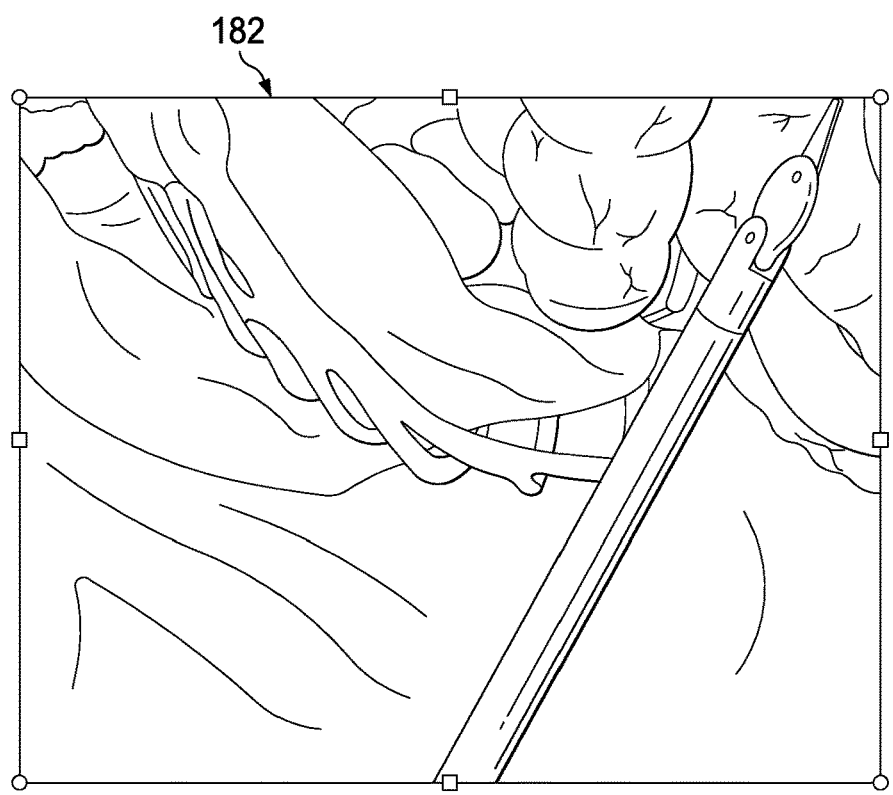
Figure 9D:
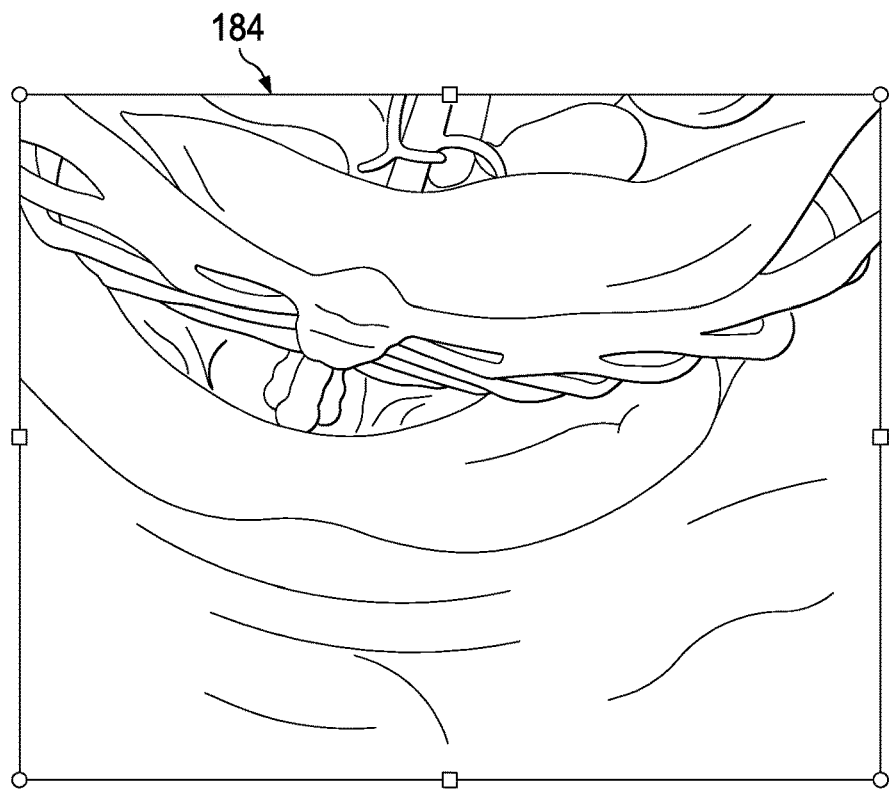
Figure 9E:
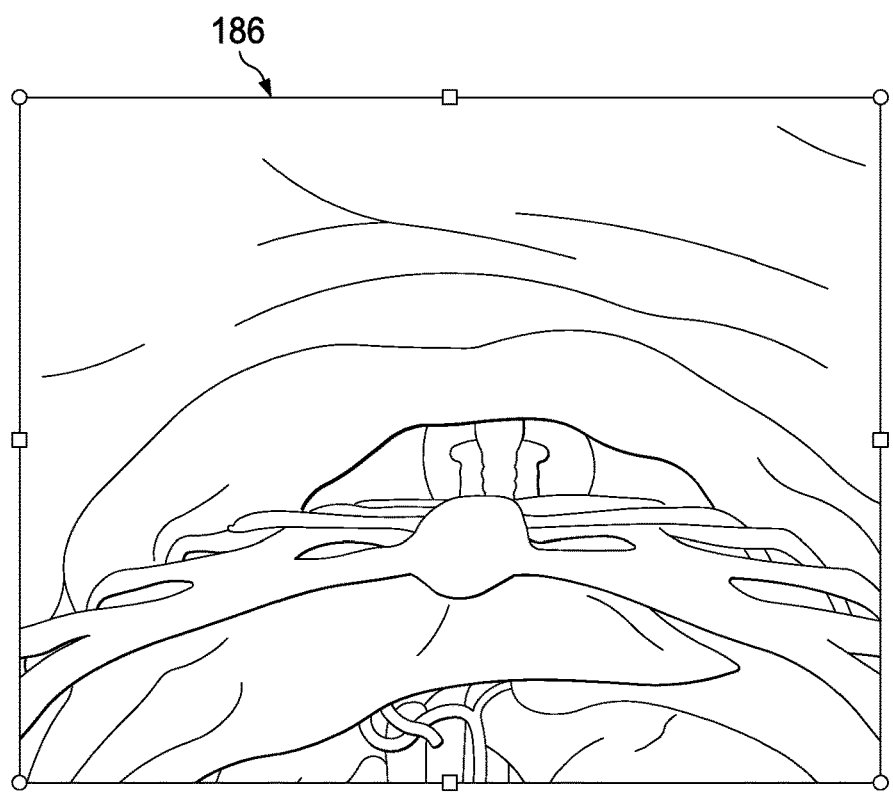

FIGS. 8 and 9A-9E illustrate a method 170 for presenting images captured while changing the direction of the field of view of an endoscopic instrument according to one embodiment of the present disclosure. This implementation employs, for example, a fixed off-axis endoscopic imaging instrument such as instrument 100. As shown in FIG. 8, a process 172 includes obtaining a stereoscopic image, such as image 178 (FIG. 9A) of a patient anatomy, with the distal end of the imaging instrument at a −30° viewing angle with respect to the insertion axis IA of the instrument shaft (as shown in FIG. 4A). A process 174 includes rotating the distal tip of the imaging instrument (for example using the method 120 described above) 180° about the insertion axis IA while capturing images of the patient anatomy. For example, images 180, 182, 184 are a series of images captured as the instrument is rotated 180° about the insertion axis IA from the −30° viewing angle (image 178) to a +30° viewing angle (image 184). Since the image 184 would appear to the viewer as being upside-down, the image 184 is flipped for presentation to the user in a process 176. An image is flipped by rotating the image 180° and displaying the fully rotated image without necessarily displaying any of the intermediate rotational stages. Image 186 depicts the flipped image 184. This implementation may minimize the use of frozen imagery, but displaying the images during the rotation of the instrument may disorient some viewers.

Figure 10:
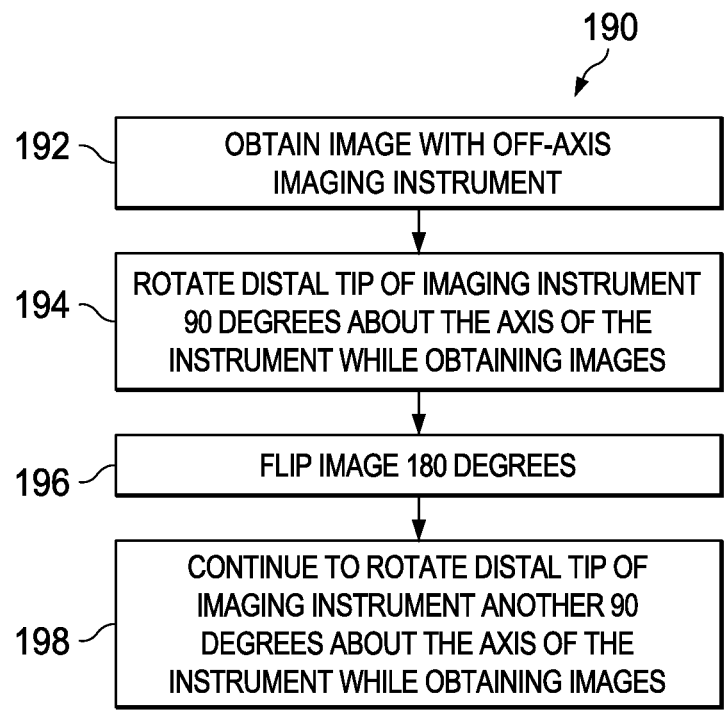
FIG. 10 illustrates a method for presenting images captured while changing the orientation of an endoscopic imaging instrument, according to another embodiment of the present disclosure.
Figure 11A:
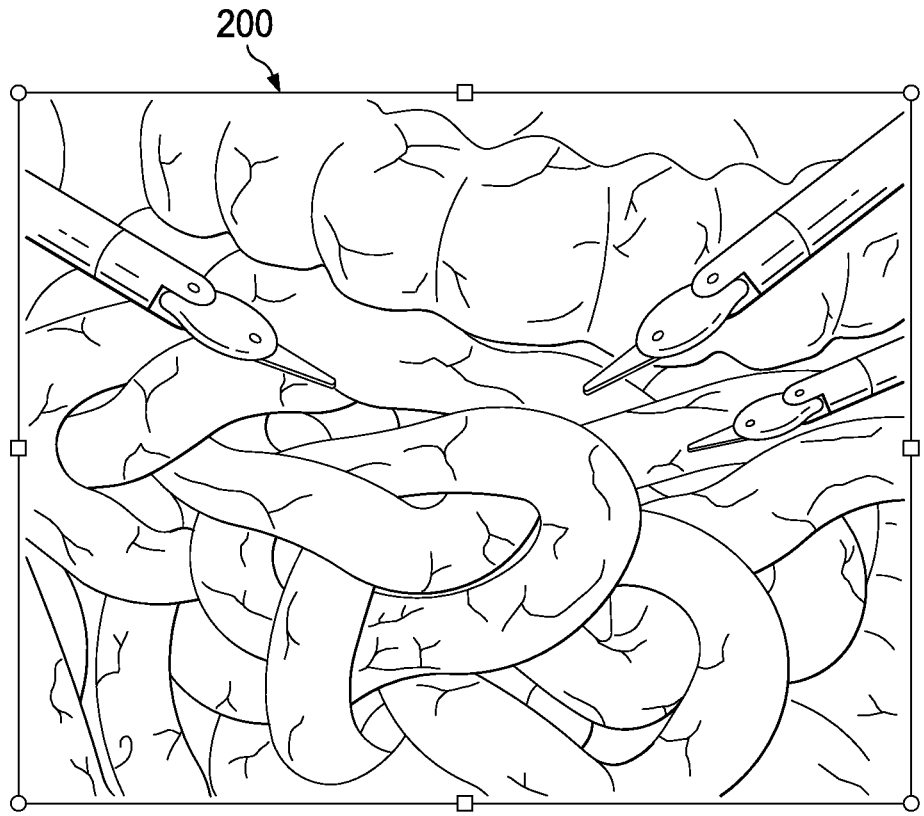
FIG. 11A-11F illustrates a series of presented images associated with the method of FIG. 10.
Figure 11B:
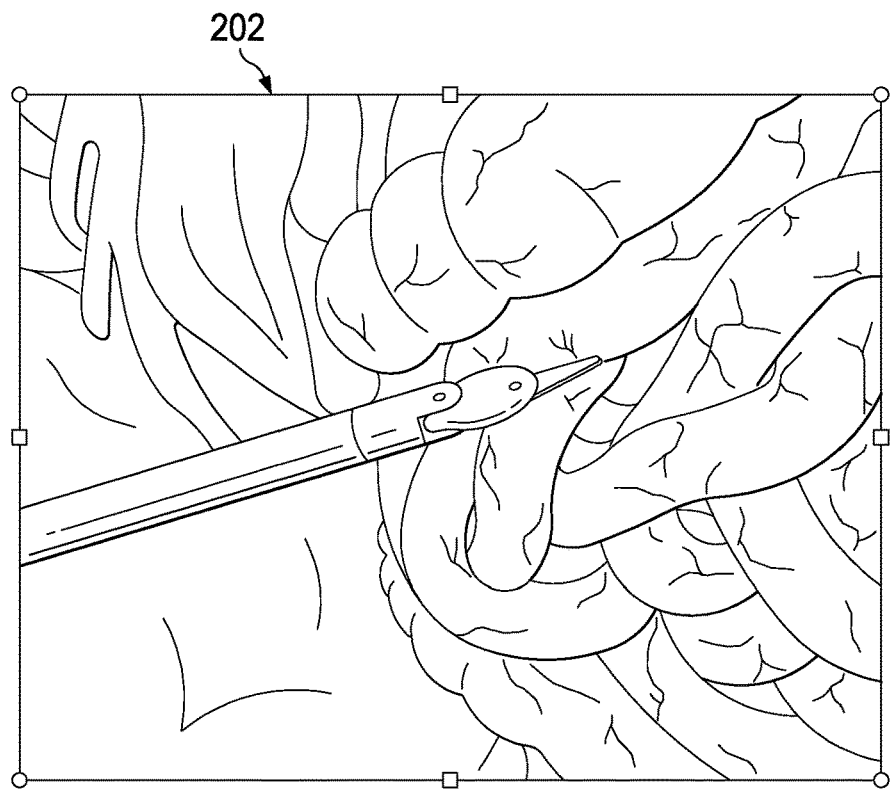
Figure 11C:
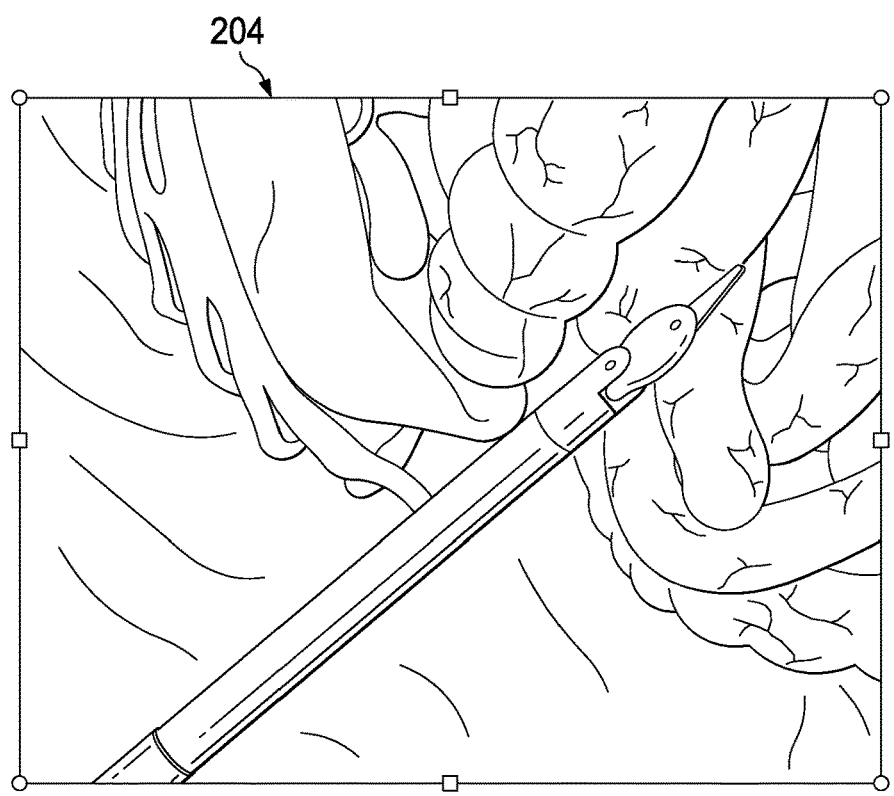
Figure 11D:
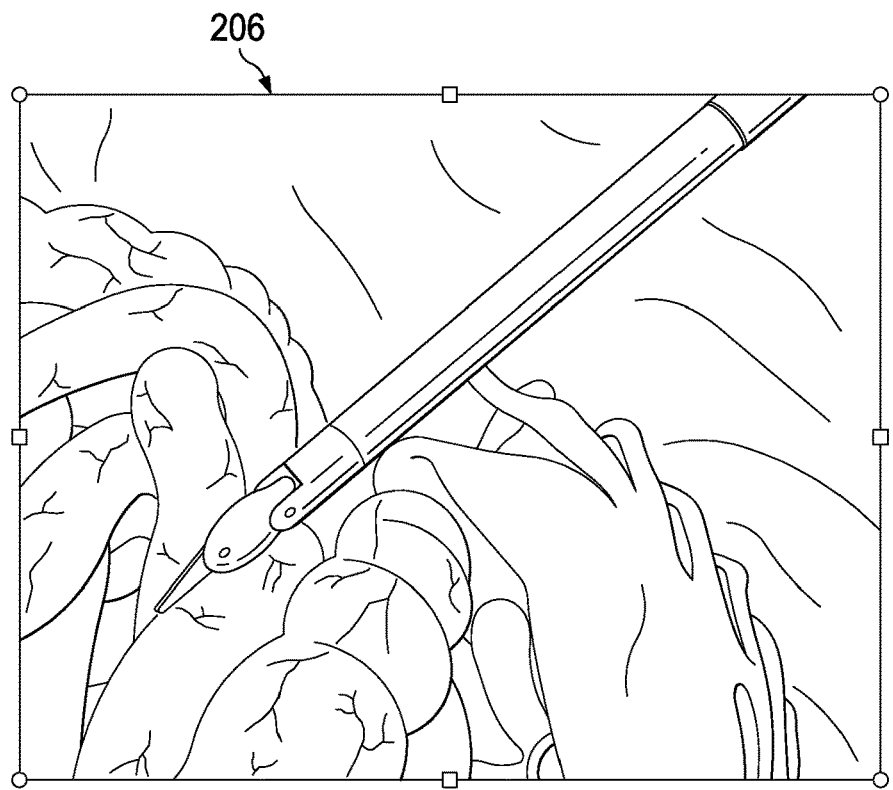
Figure 11E:
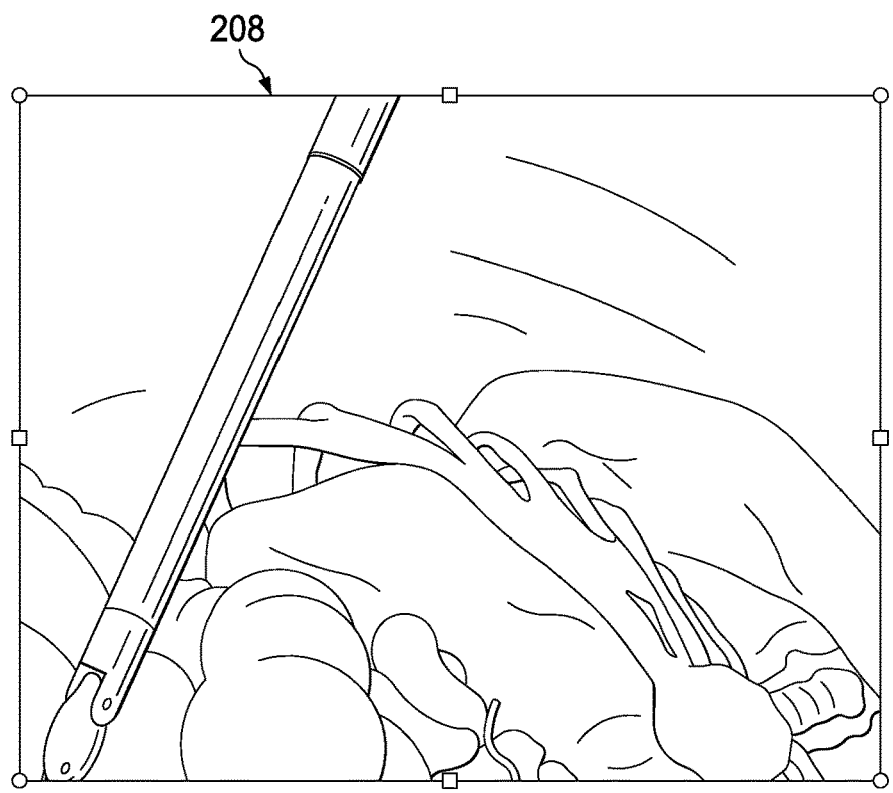
Figure 11F:
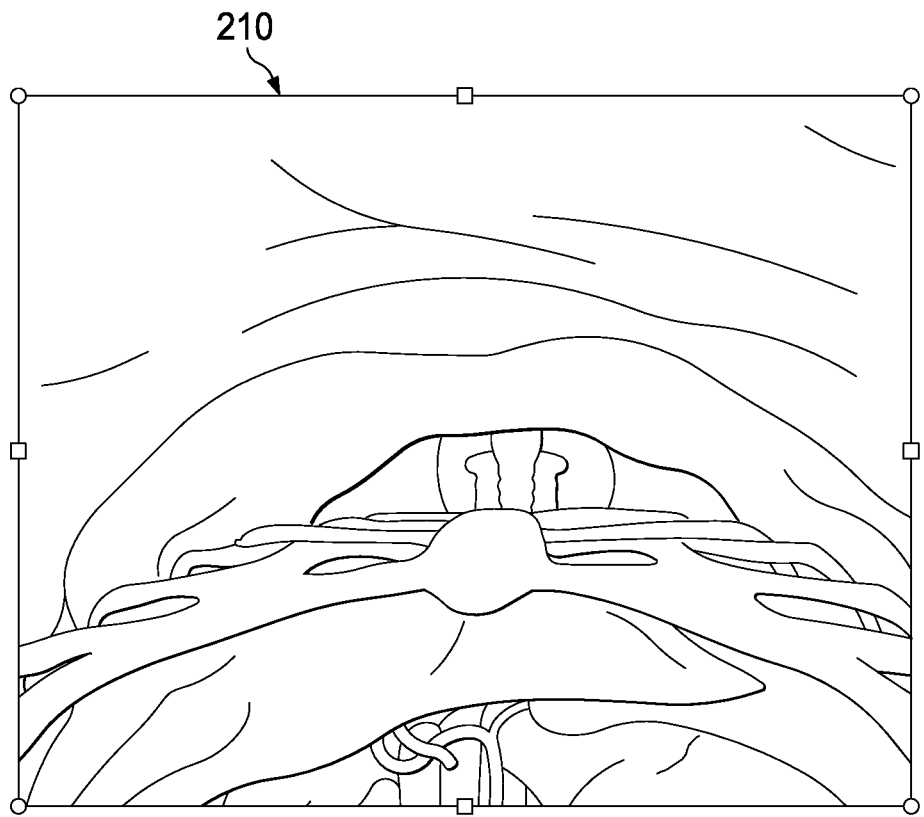

FIGS. 10 and 11A-11F illustrate a method 190 for presenting images captured while changing the direction of the field of view of an endoscopic instrument according to another embodiment of the present disclosure. This implementation employs, for example, a fixed off-axis endoscopic imaging instrument such as instrument 100. As shown in FIG. 10, a process 192 includes obtaining a stereoscopic image, such as image 200 (one eye shown, other eye view is omitted to simplify the figures) (FIG. 11A) of a patient anatomy, with the distal end of the imaging instrument at a −30° viewing angle with respect to the insertion axis IA of the instrument shaft (as shown in FIG. 4A). A process 194 includes rotating the distal tip of the imaging instrument (for example using the method 120 described above) 90° about the insertion axis IA while capturing images of the patient anatomy. For example, images 202, 204 are a series of images captured as the instrument is rotated 90° about the insertion axis IA. The image 204 is flipped for presentation to the user in a process 196. An image is flipped by rotating the image 180° and displaying the fully rotated image without necessarily displaying any of the intermediate rotational stages. Image 206 depicts the flipped image 204. A process 198 includes further rotating the distal tip of imaging instrument 90° about the insertion axis IA (in the same rotational direction as in process 194) while capturing images of the patient anatomy. For example, images 208 and 210 are a series of images captured as the instrument is further rotated 90° about the insertion axis IA. This implementation may minimize the use of frozen imagery and avoids any presentation of an image that appears upside down to a viewer. The flip transition may, however, be disruptive to some viewers.

Figure 12:
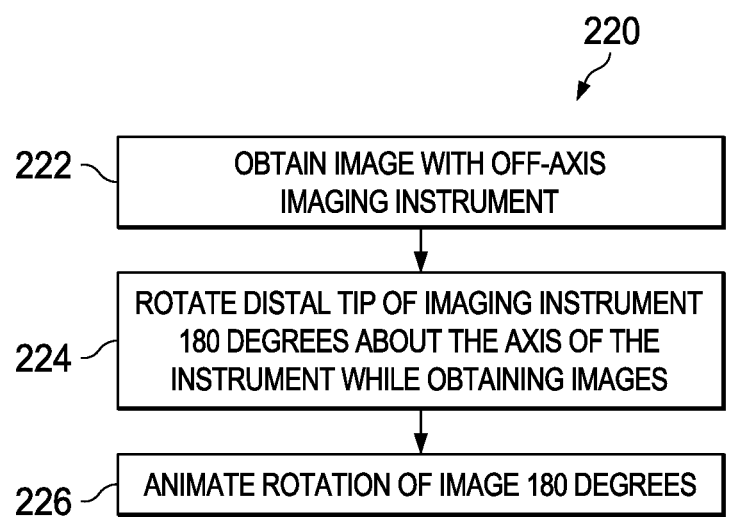
FIG. 12 illustrates a method for presenting images captured while changing the orientation of an endoscopic imaging instrument, according to another embodiment of the present disclosure.
Figure 13A:
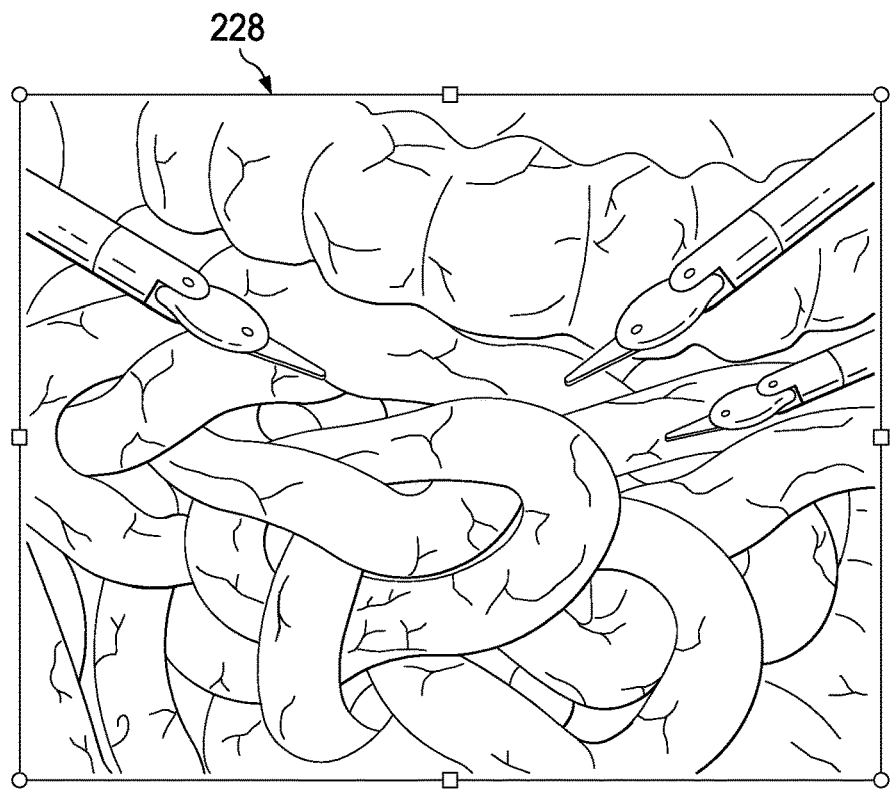
FIG. 13A-13E illustrates a series of presented images associated with the method of FIG. 12.
Figure 13B:
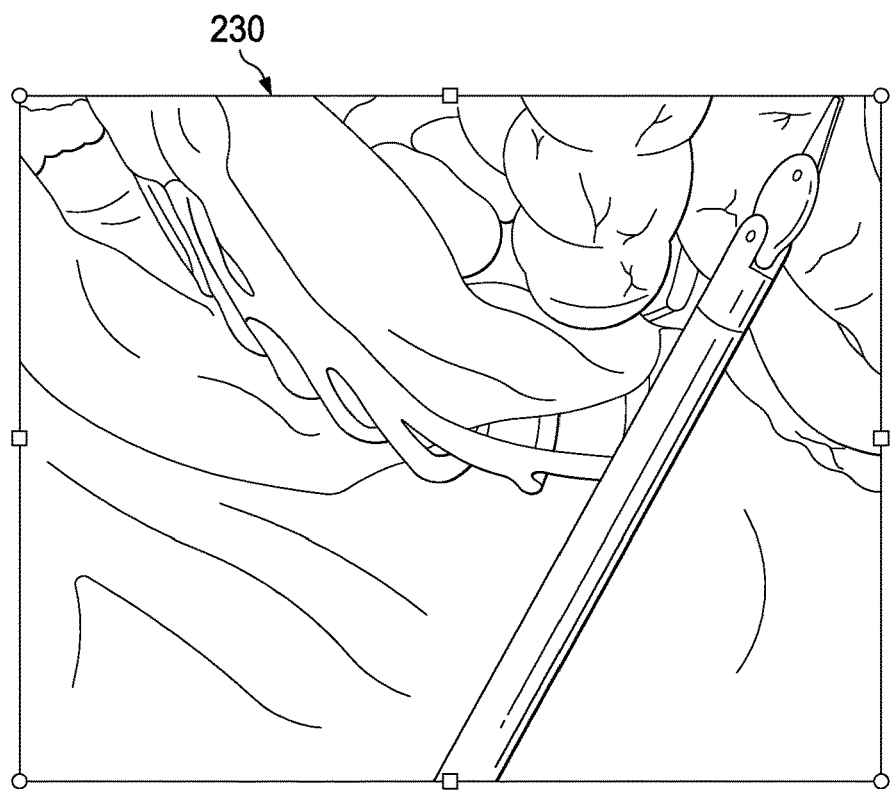
Figure 13C:
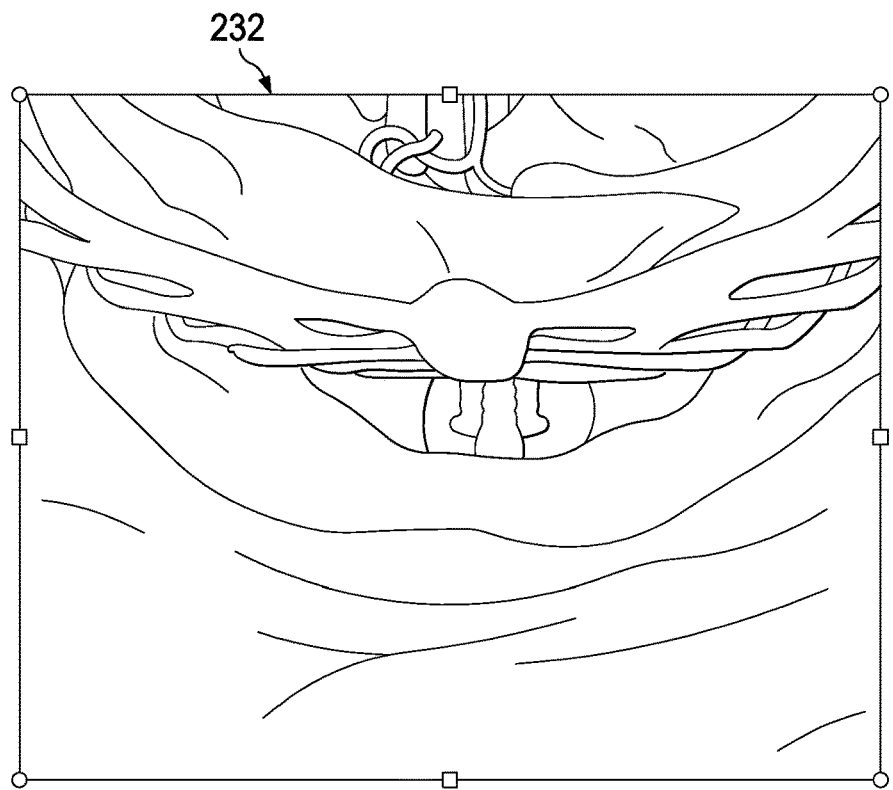
Figure 13D:
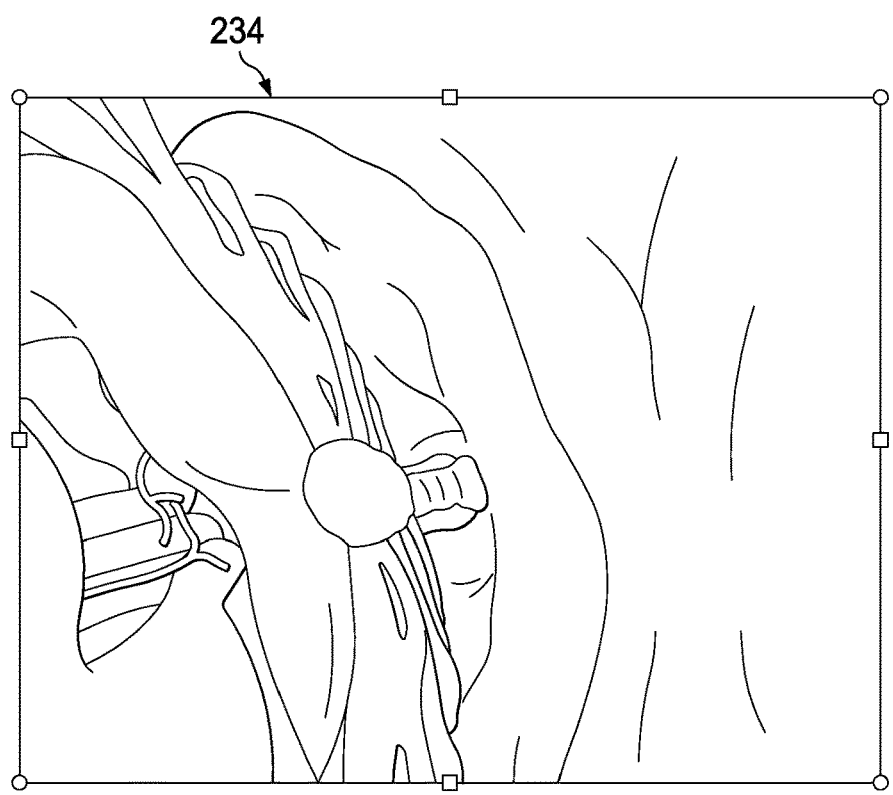
Figure 13E:
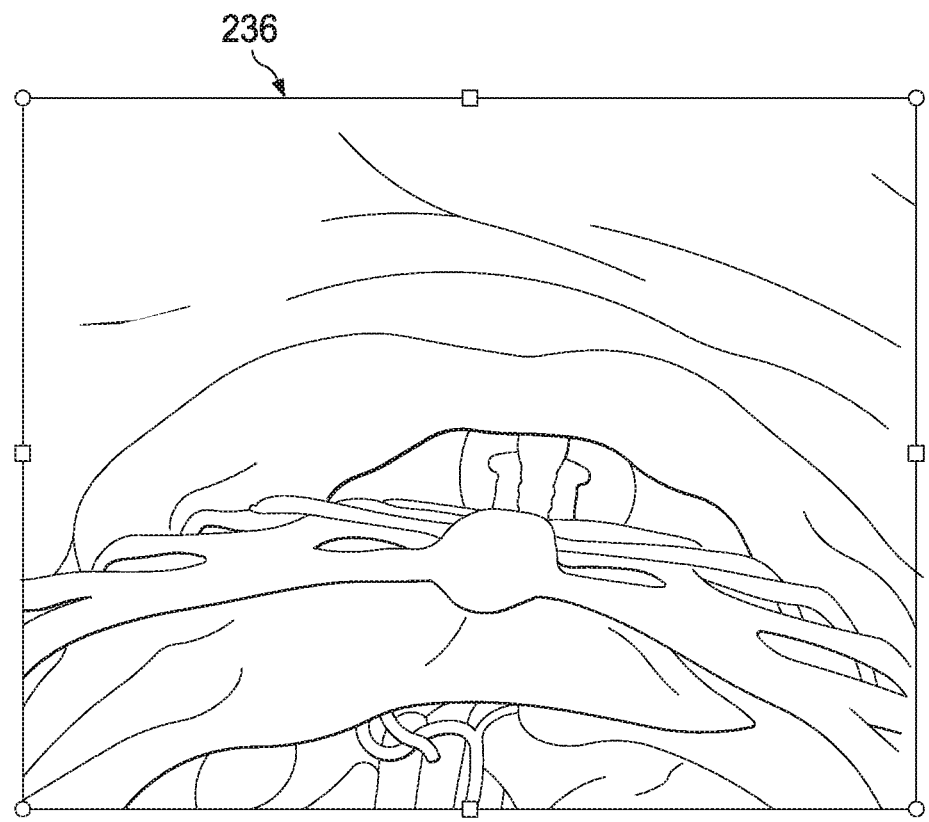

FIGS. 12 and 13A-13E illustrate a method 220 for presenting images captured while changing the direction of the field of view of an endoscopic instrument according to another embodiment of the present disclosure. This implementation employs, for example, a fixed off-axis endoscopic imaging instrument similar to instrument 100 but with monocular imaging, rather than stereo imaging. As shown in FIG. 12, a process 222 includes obtaining an image, such as image 228 (FIG. 13A) of a patient anatomy, with the distal end of the imaging instrument at a −30° viewing angle with respect to the insertion axis IA of the instrument shaft (as shown in FIG. 4A). A process 224 includes rotating the distal tip of the imaging instrument (for example using the method 120 described above) 180° about the insertion axis IA while capturing images of the patient anatomy. For example, images 230, 232 are a series of images captured as the instrument is rotated 180° about the insertion axis IA. The image 232 is rotated for presentation to the user in a process 226 by displaying animated intermediate images of the rotation, such as intermediate image 234. Image 236 depicts the final stage of 180° rotation of image 232. This implementation may avoid the use of frozen imagery and potentially confusing image flips. In this implementation, the animated rotation may be disorienting to some viewers and the use of stereoscopic imaging may be precluded.

Figure 14:
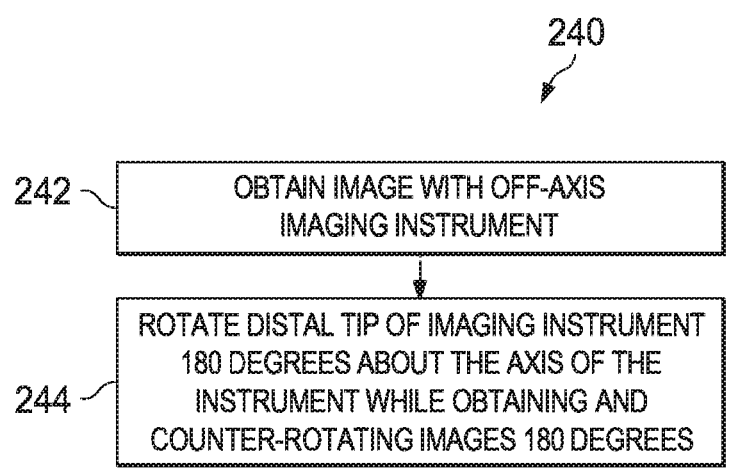
FIG. 14 illustrates a method for presenting images captured while changing the orientation of an endoscopic imaging instrument, according to another embodiment of the present disclosure.
Figure 15A:
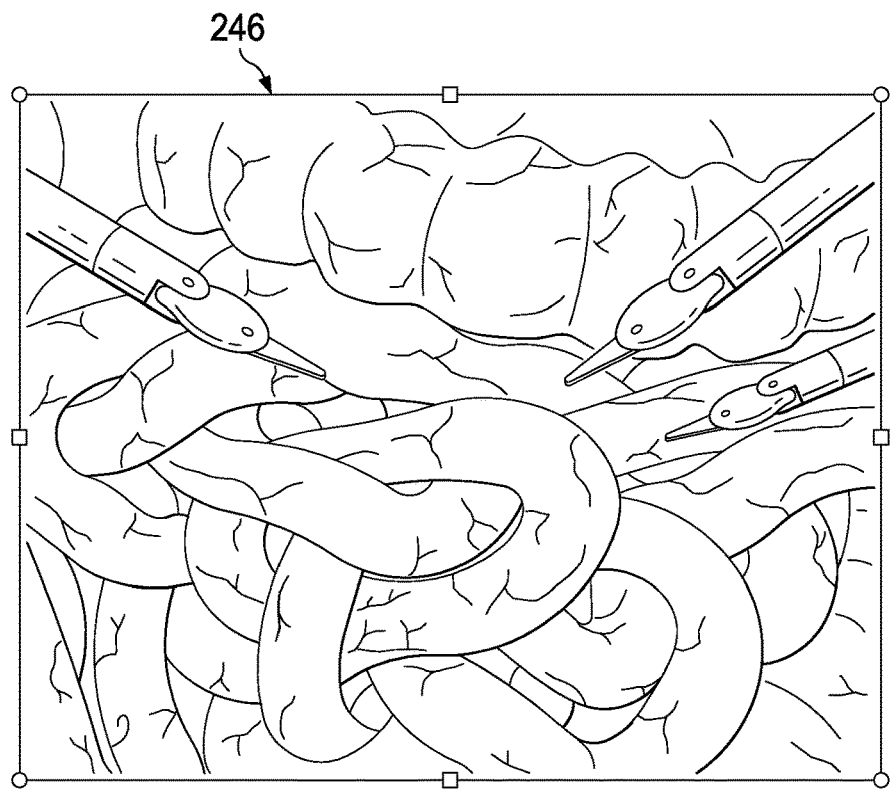
FIG. 15A-15F illustrates a series of presented images associated with the method of FIG. 14.
Figure 15B:
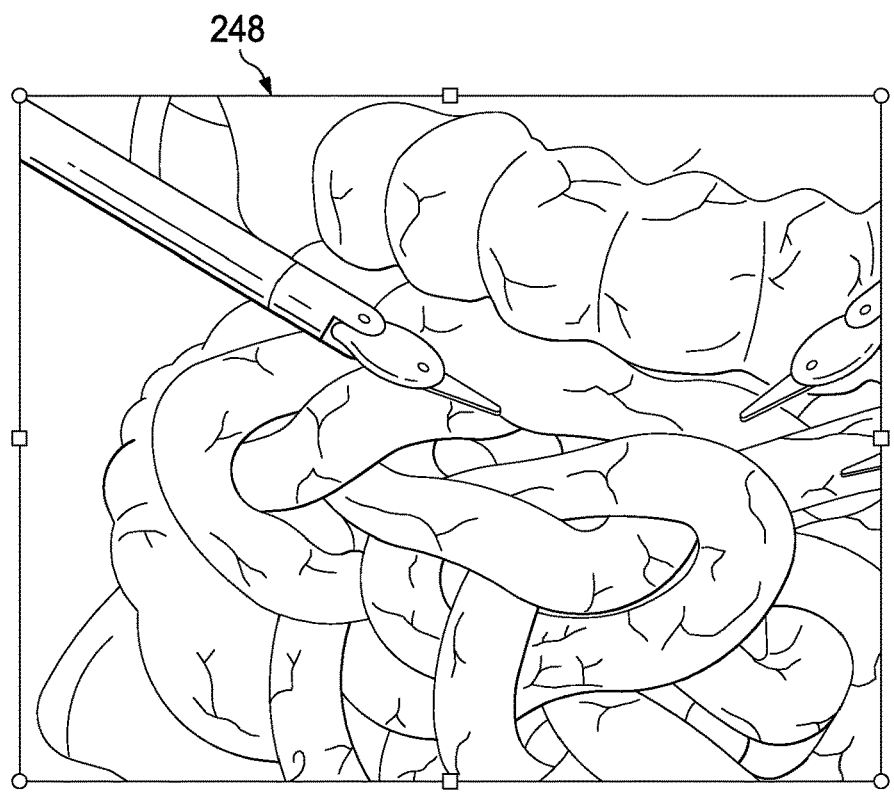
Figure 15C:
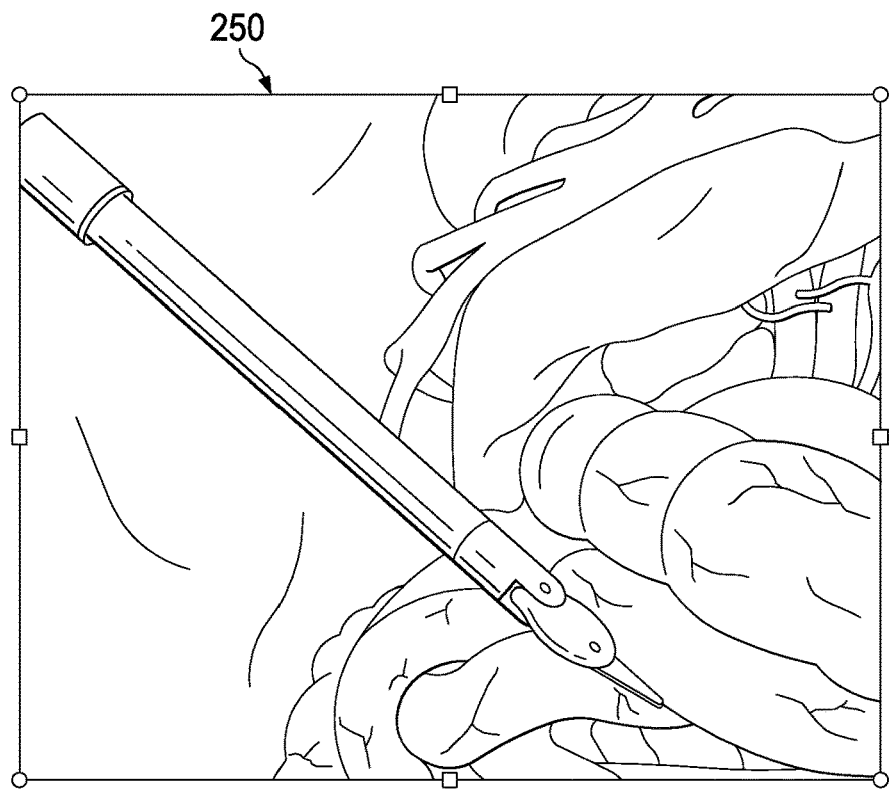
Figure 15D:
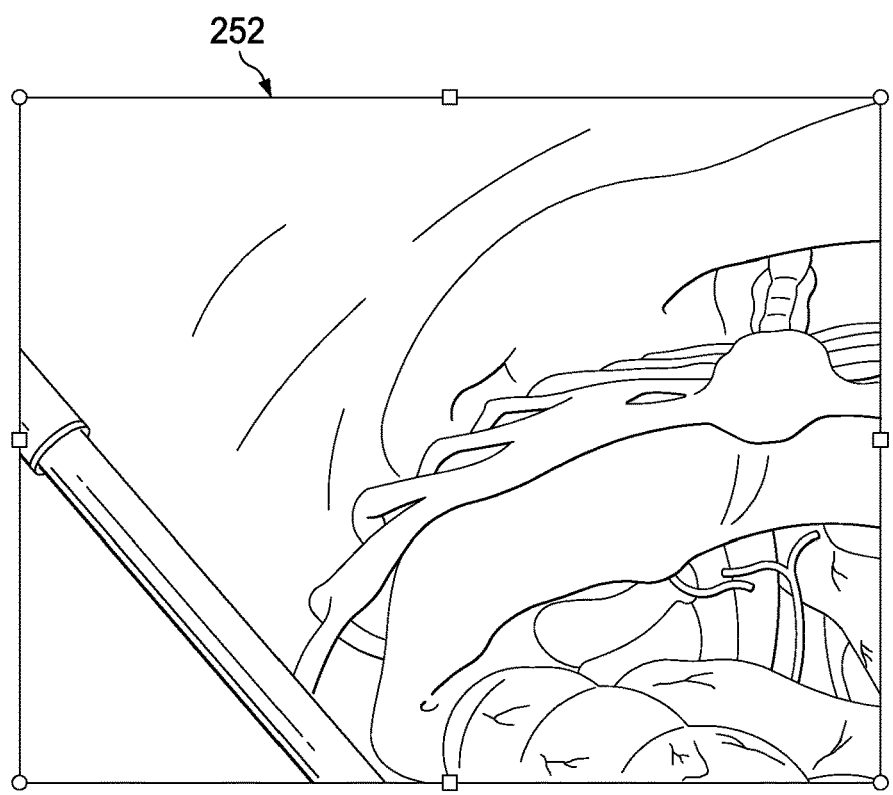
Figure 15E:
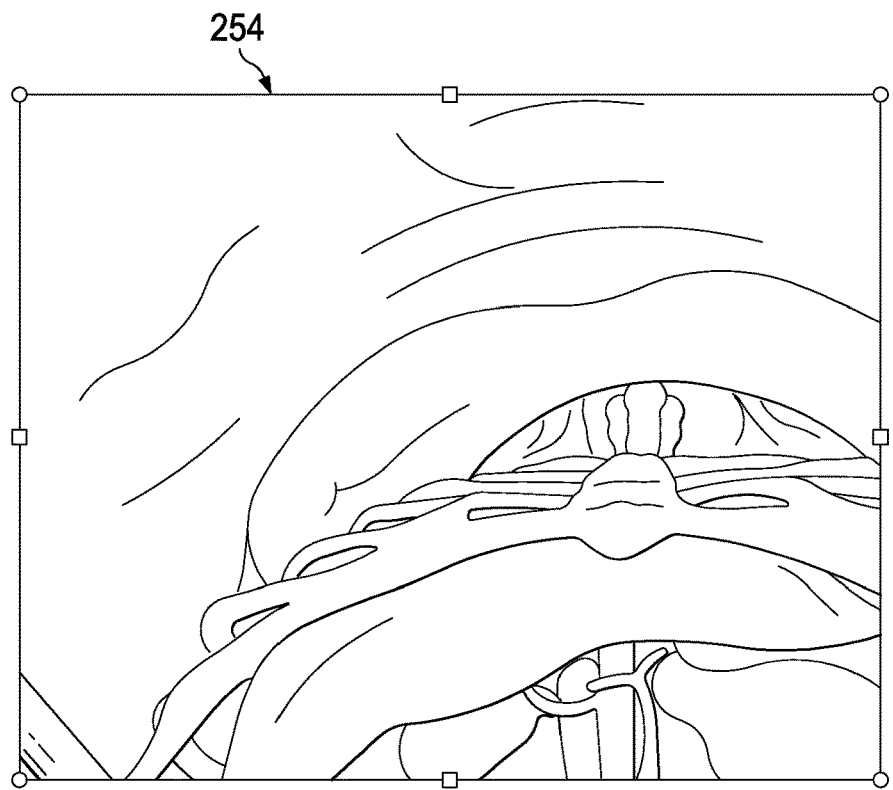
Figure 15F:
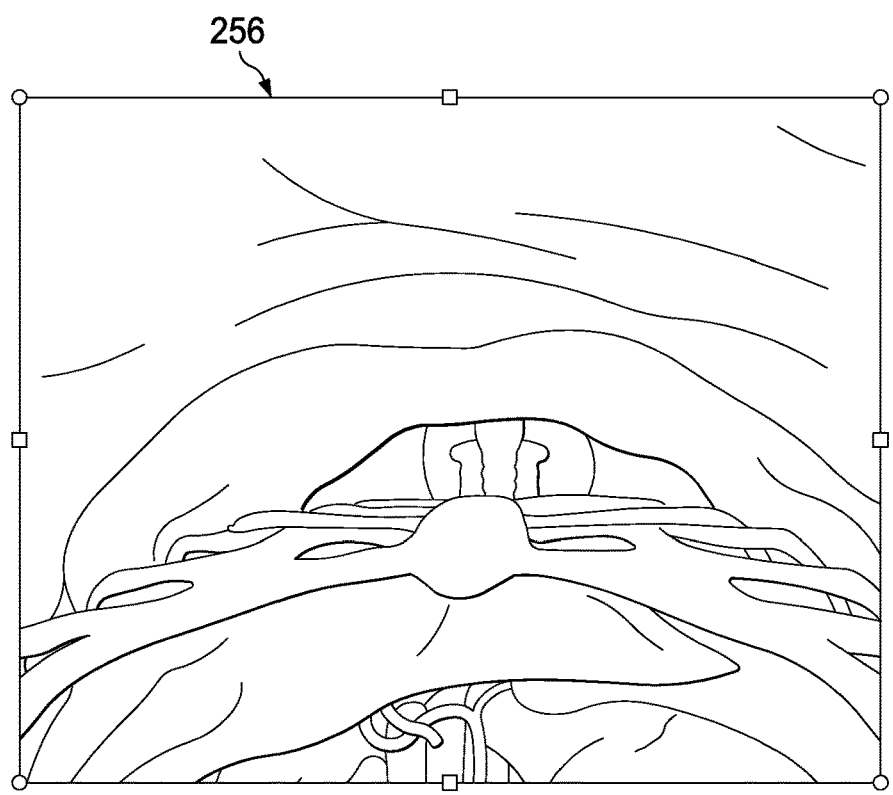

FIGS. 14 and 15A-15F illustrate a method 240 for presenting images captured while changing the direction of the field of view of an endoscopic instrument according to another embodiment of the present disclosure. This implementation employs, for example, a fixed off-axis endoscopic imaging instrument similar to instrument 100 but with monocular imaging, rather than stereo imaging. As shown in FIG. 14, a process 242 includes obtaining an image, such as image 246 (FIG. 15A) of a patient anatomy, with the distal end of the imaging instrument at a −30° viewing angle with respect to the insertion axis IA of the instrument shaft (as shown in FIG. 4A). A process 244 includes rotating the distal tip of the imaging instrument (for example using the method 120 described above) 180° about the insertion axis IA while capturing images of the patient anatomy. At the same time, that the instrument is rotating, the captured images are counter-rotated 180° with animated video image rotation. For example, images 248-256 are a series of images captured as the instrument is rotated 180° about the insertion axis IA and counter-rotated 180°. Image 256 depicts the final stage of 180° instrument rotation and image counter-rotation. This implementation may avoid the use of frozen imagery, preserve spatial orientation, and closely approximate the idealized transition of method 150 described above. In this implementation, a sensor may be provided to sense scope roll. Sensing the roll may permit synchronization with the animated video rotation. In this implementation, the use of stereoscopic imaging may be precluded. Additionally, this implementation may be used when the instrument 100 is coupled to the teleoperational system because the control system for the teleoperational system controls both the roll of the endoscope and the logical roll of the presented images. If the instrument 100 is in manual use without attachment to the teleoperational system, a similar implementation may be achieved by sensing roll with an alternative sensor. For example, a sensor on the instrument may sense roll of the adaptor 106 with respect to the handle or an accelerometer(s) may be used to sense the roll angle of the endoscope body relative to gravity.

Figure 16:
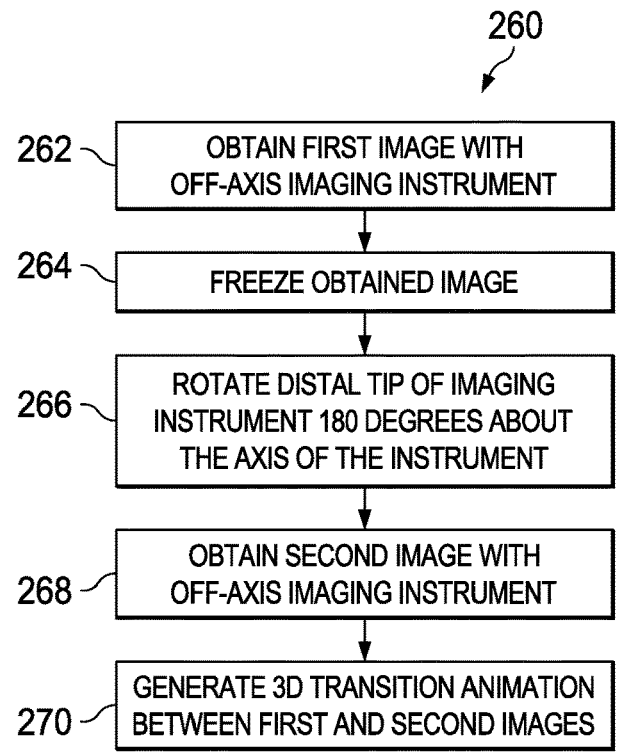
FIG. 16 illustrates a method for presenting images captured while changing the orientation of an endoscopic imaging instrument, according to another embodiment of the present disclosure.
Figure 17A:
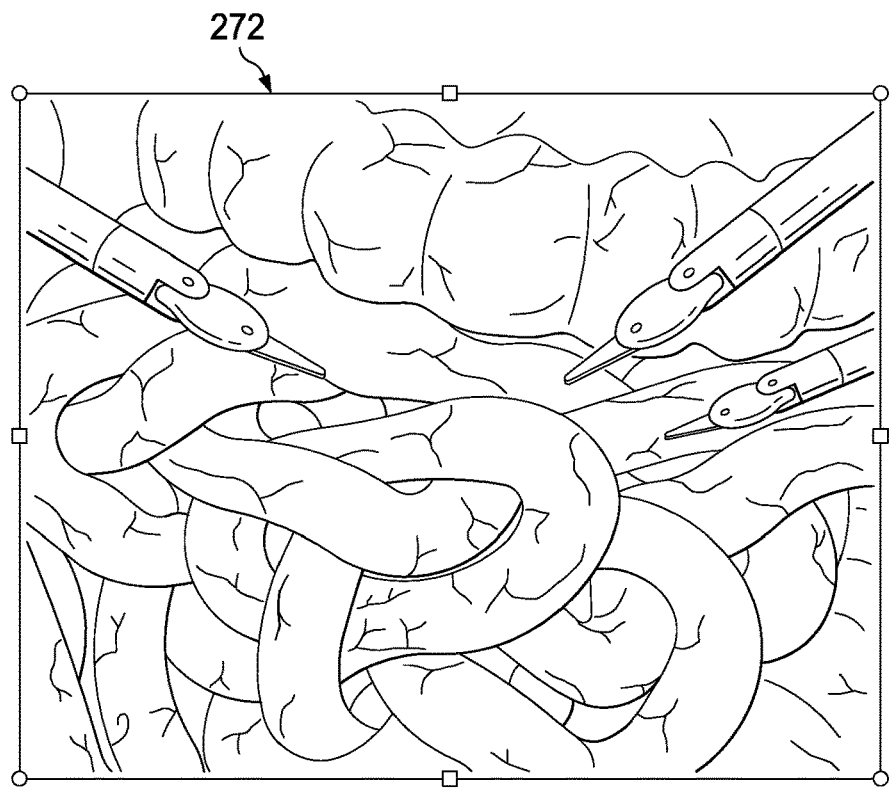
FIG. 17A-17C illustrates a series of presented images associated with the method of FIG. 16.
Figure 17B:
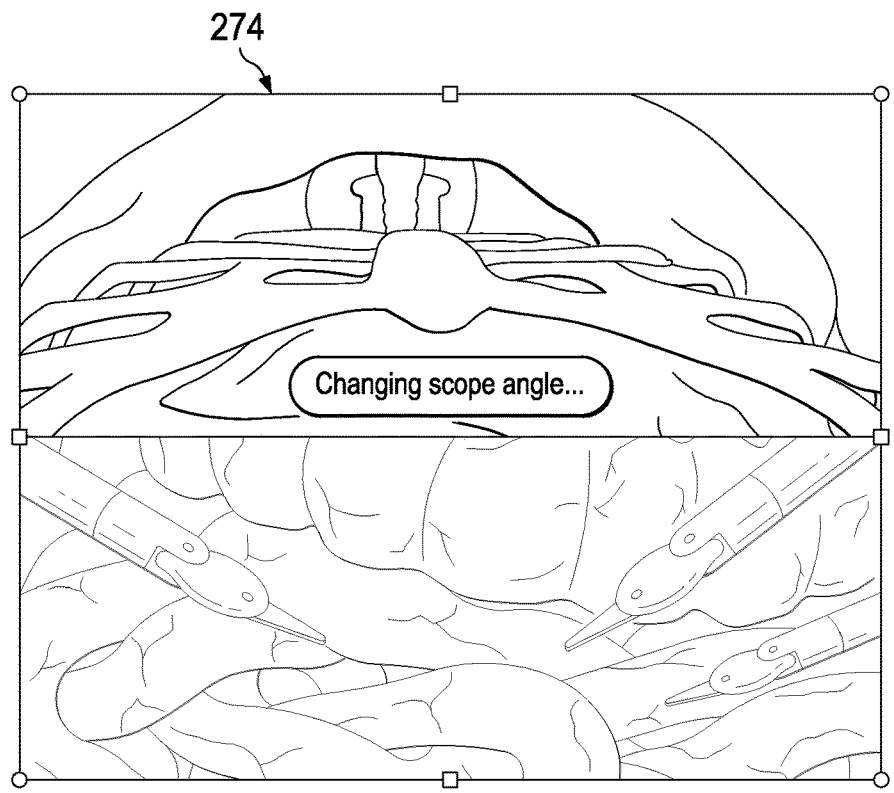
Figure 17C:
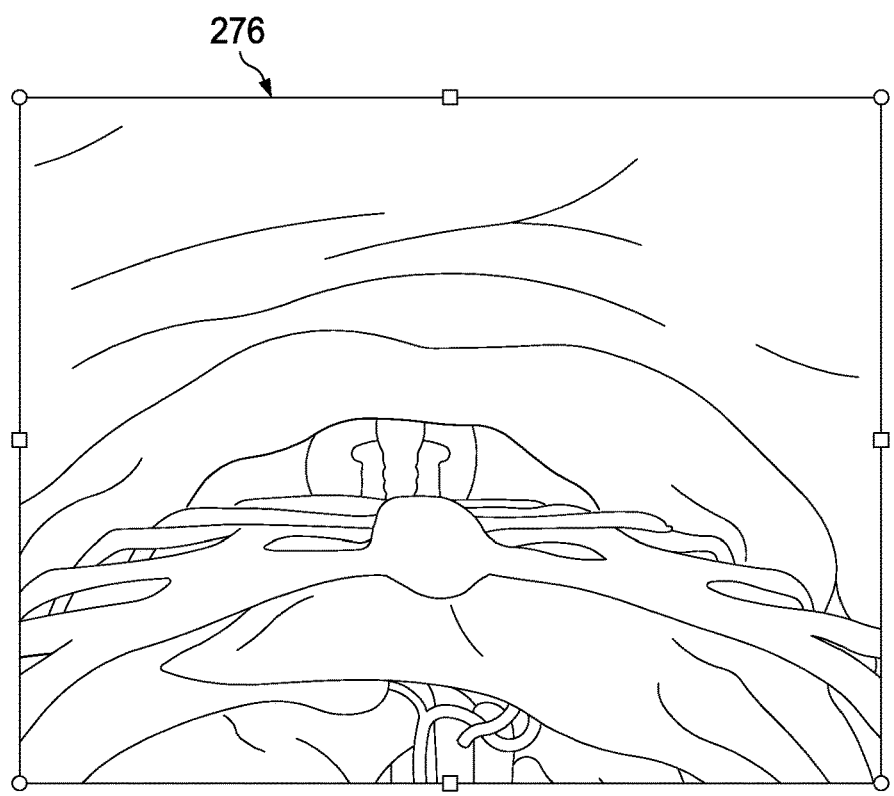

FIGS. 16 and 17A-17C illustrate a method 260 for presenting images captured while changing the direction of the field of view of an endoscopic instrument according to another embodiment of the present disclosure. This implementation employs, for example, a fixed off-axis endoscopic imaging instrument such as instrument 100. As shown in FIG. 16, a process 262 includes obtaining an image, such as image 272 (FIG. 17A) of a patient anatomy, with the distal end of the imaging instrument at a −30° viewing angle with respect to the insertion axis IA of the instrument shaft (as shown in FIG. 4A). A process 264 includes freezing the obtained image 272. A process 266 includes rotating the distal tip of the imaging instrument (for example using the method 120 described above) 180° about the insertion axis IA. A process 268 includes obtaining an image, such as image 276 (FIG. 17C) of the patient anatomy, with the distal end of the imaging instrument at a +30° viewing angle with respect to the insertion axis IA of the instrument shaft (as shown in FIG. 4B). A process 270 includes generating a three-dimensional transition animation between the images 272, 276 as shown in image 274. This transition animation presents the upward and downward images mapped onto the faces of a rotating box. This implementation may closely approximate the idealized transition method 150 described above and may preserve the viewer's spatial orientation. This implementation may utilize a three-dimensional video transition effect.

Figure 18:
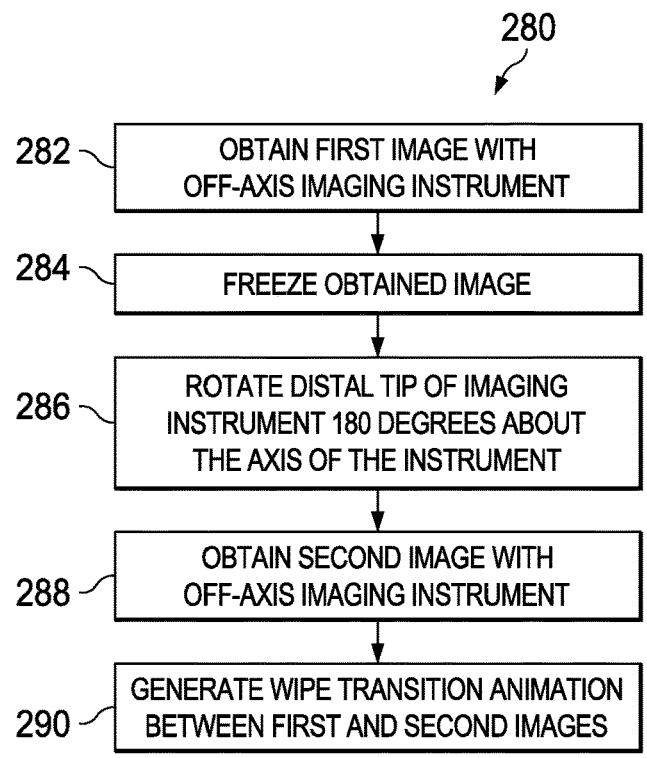
FIG. 18 illustrates a method for presenting images captured while changing the orientation of an endoscopic imaging instrument, according to another embodiment of the present disclosure.
Figure 19A:
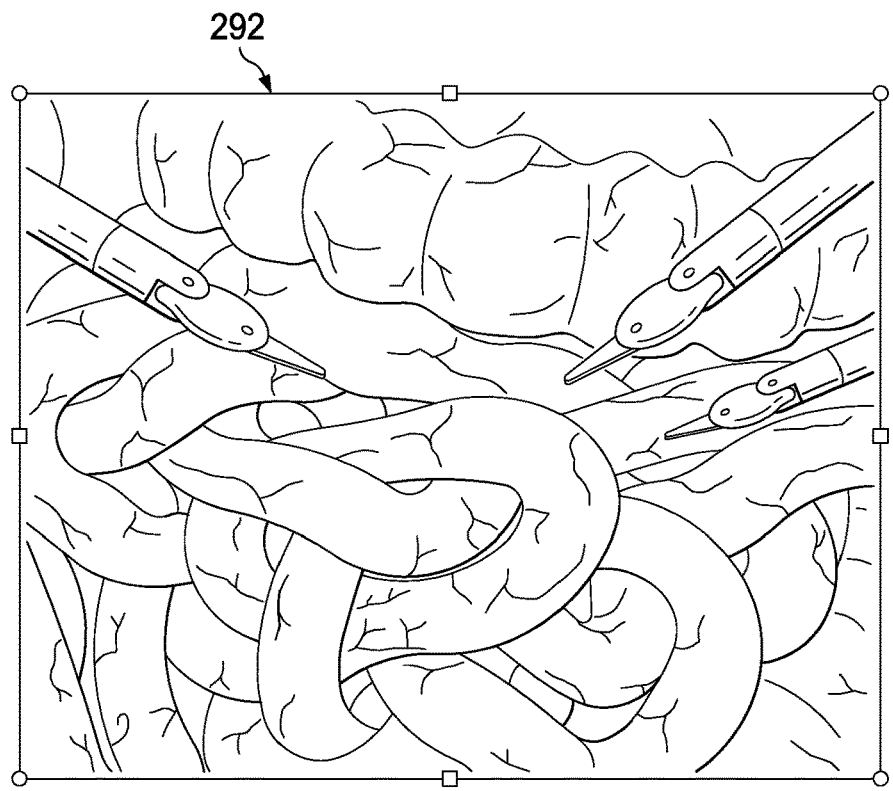
FIG. 19A-19D illustrates a series of presented images associated with the method of FIG. 18.
Figure 19B:
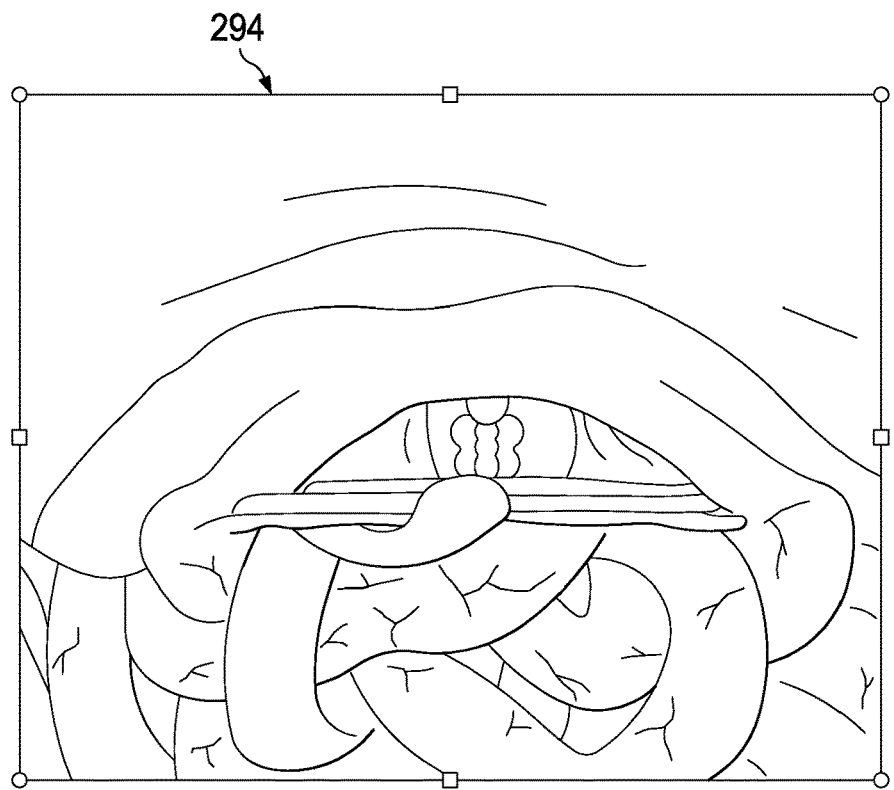
Figure 19C:
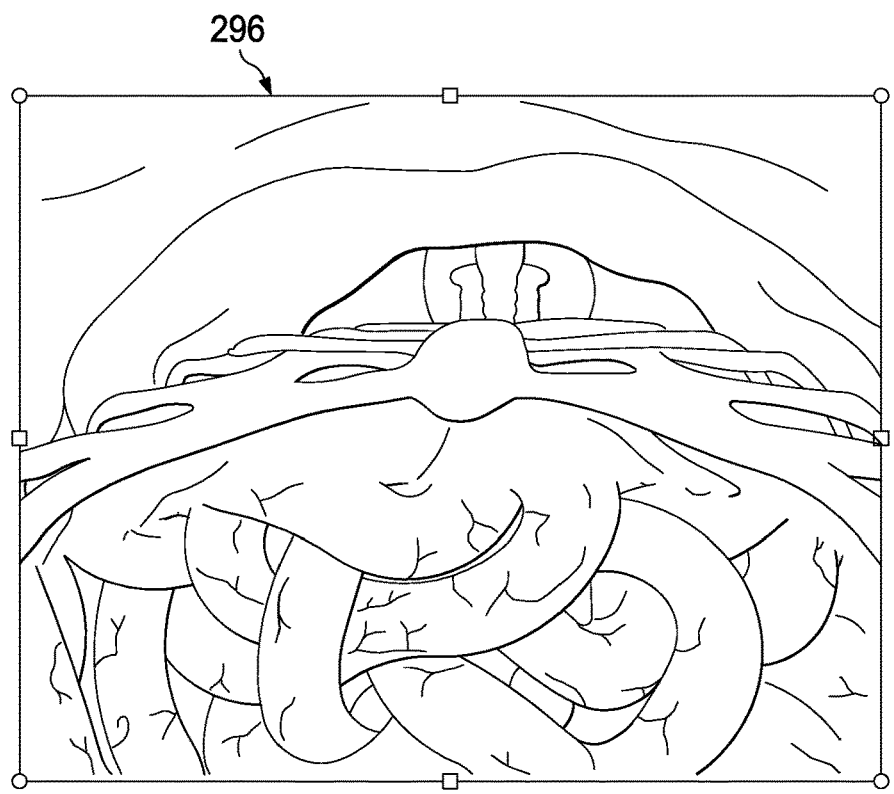
Figure 19D:
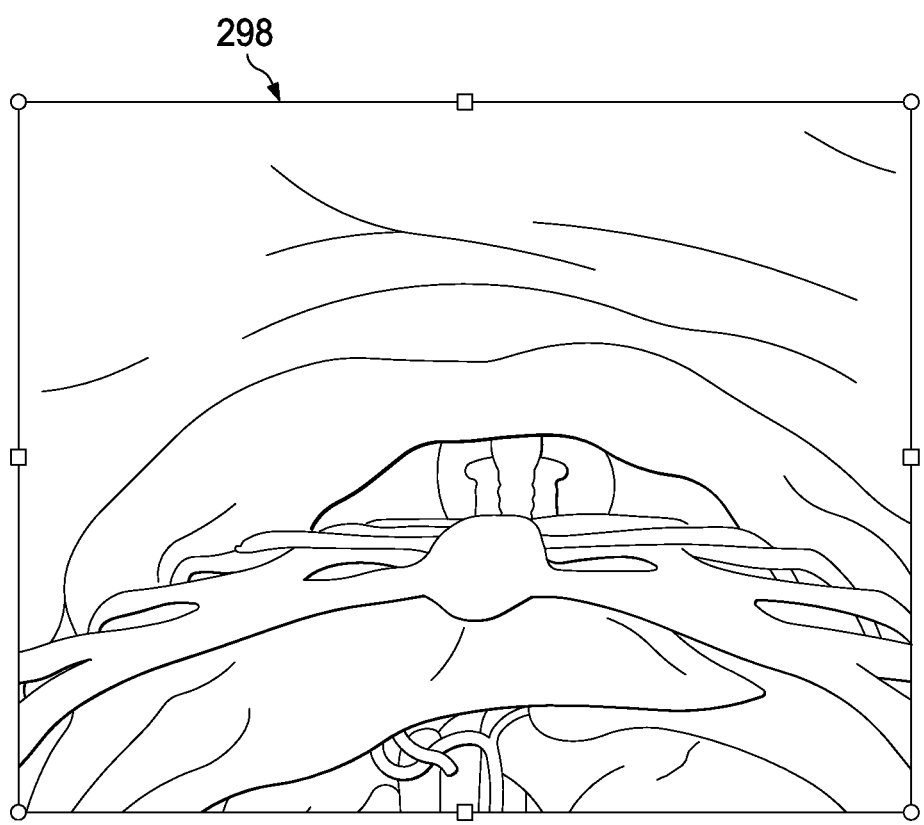

FIGS. 18 and 19A-19D illustrate a method 280 for presenting images captured while changing the direction of the field of view of an endoscopic instrument according to another embodiment of the present disclosure. This implementation employs, for example, a fixed off-axis endoscopic imaging instrument such as instrument 100. As shown in FIG. 18, a process 282 includes obtaining an image, such as image 292 (FIG. 19A) of a patient anatomy, with the distal end of the imaging instrument at a −30° viewing angle with respect to the insertion axis IA of the instrument shaft (as shown in FIG. 4A). A process 284 includes freezing the obtained image 292. A process 286 includes rotating the distal tip of the imaging instrument (for example using the method 120 described above) 180° about the insertion axis IA. A process 288 includes obtaining an image, such as image 298 (FIG. 19D) of the patient anatomy, with the distal end of the imaging instrument at a +30° viewing angle with respect to the insertion axis IA of the instrument shaft (as shown in FIG. 4B). A process 290 includes generating a wipe transition animation between the images 292, 298 as shown in images 294 and 296. The directionality of the wipe transition corresponds to the change in the viewing angle (i.e., either wipe top-to-bottom when changing 30° up to 30° down or wipe bottom-to-top when changing 30° down to 30° up). This implementation may allow for the use of stereoscopic imaging. This implementation may utilize a video wipe transition effect, but in alternative embodiments may use other animated transition effects.

In alternative embodiments, other techniques for presenting images captured while changing the direction of the field of view may be used. For example, during the physical roll procedure for the imaging instrument, a non-surgical image may be displayed. For example, the non-surgical image may be a blank mono-color pane, a graphic, a logo, or an alpha-numeric message. Alternatively, during the physical roll procedure for the imaging instrument, a freeze frame of a surgical image may be displayed.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Also note that image flips and rotations may be performed in the video processing pipeline by hardware or software. Alternatively, image flips and rotations may be effected by changing the orientation of the image on the display device by changing the horizontal and/or vertical raster directions which has the advantage of avoiding additional delays. this can be achieved in some LCD controllers by programmatically updating control registers.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical imaging system comprising:
    a teleoperational assembly; and
    a processing unit including one or more processors, wherein the processing unit is configured for:
        receiving a roll position indicator for an imaging instrument coupled to the teleoperational assembly, wherein the imaging instrument has a view angle other than 0° relative to an optical axis of the imaging instrument, and wherein the imaging instrument is a stereoscopic imaging instrument including first and second image sources;
        obtaining first image data from the imaging instrument coupled to the teleoperational assembly at a first roll position;
        obtaining subsequent image data from the imaging instrument coupled to the teleoperational assembly at a second roll position; and
        responsive to a roll movement of the imaging instrument between the first and second roll positions, transitioning between presentation of the first image data on a user display and presentation of the subsequent image data on the user display, wherein the transition between the presentation of the first image data and the presentation of the subsequent image data includes changing a position of presentation of the first and second image sources of the stereoscopic imaging instrument.

2. The medical imaging system of claim 1 wherein the transition between presentation of the first image data and presentation of the subsequent image data is continuous.

3. The medical imaging system of claim 1 wherein the transition between presentation of the first image data and presentation of the subsequent image data is discrete.

4. The medical imaging system of claim 1 wherein transitioning between presentation of the first image data on the user display and presentation of the subsequent image data on the user display includes generating a rotated image from one of the first or subsequent image data based upon the roll position indicator.

5. The medical imaging system of claim 4 wherein the rotated image is rotated approximately 180°.

6. The medical imaging system of claim 1 wherein the processing unit is further configured for receiving instructions to rotate the imaging instrument between the first and second roll positions.

7. The medical imaging system of claim 6 wherein a roll angle between the first and second roll positions is approximately 180°.

8. The medical imaging system of claim 1 wherein the imaging instrument has a view angle of approximately 30°.

9. The medical imaging system of claim 1 wherein the transition between presentation of the first image data and presentation of the subsequent image data further includes rotating a first image generated from the first image data 180° and rotating a second image generated from the subsequent image data 180°.

10. The medical imaging system of claim 1 wherein the processing unit is further configured for generating a sequence of images including a rotated image from one of the first or subsequent image data and a non-rotated image from the other of the first or subsequent image data.

11. The medical imaging system of claim 10 wherein the processing unit is further configured for obtaining third image data from the imaging instrument coupled to the teleoperational assembly at a third roll position between the first and second roll positions and the sequence of images includes an image generated from the third image data.

12. The medical imaging system of claim 11 wherein the processing unit is further configured to rotate the image generated from the third image data.

13. The medical imaging system of claim 10 wherein the sequence of images includes a three-dimensional transition animation or a wipe transition animation.

14. The medical imaging system of claim 1 wherein the processing unit is further configured for generating a rotation animation from one of the first or subsequent image data based upon the roll position indicator.

15. The medical imaging system of claim 1 further comprising the imaging instrument, and a sensor coupled to the imaging instrument, the sensor configured to provide the roll position indicator.

16. A non-transitory machine-readable medium comprising a plurality of machine-readable instructions which when executed by one or more processors are adapted to cause the one or more processors to perform a method comprising:
  receiving a roll position indicator for an imaging instrument coupled to a teleoperational assembly, wherein the imaging instrument has a view angle greater than 0° relative to an optical axis of the imaging instrument, and wherein the imaging instrument is a stereoscopic imaging instrument including first and second image sources;
  obtaining first image data from the imaging instrument coupled to the teleoperational assembly at a first roll position;
  obtaining subsequent image data from the imaging instrument coupled to the teleoperational assembly at a second roll position; and
  responsive to a roll movement of the imaging instrument between the first and second roll positions, transitioning between presentation of the first image data on a user display and presentation of the subsequent image data on the user display, wherein the transition between the presentation of the first image data and the presentation of the subsequent image data includes changing a position of presentation of the first and second image sources of the stereoscopic imaging instrument.

17. The non-transitory machine-readable medium of claim 16 wherein the method further comprises generating a rotated image from the first or subsequent image data based upon the roll position indicator.

18. The non-transitory machine-readable medium of claim 16 wherein the method further comprises generating a sequence of images including a rotated image from one of the first or subsequent image data and a non-rotated image from the other of the first or subsequent image data.

19. The non-transitory machine-readable medium of claim 18, wherein the method further comprises obtaining third image data from the imaging instrument coupled to the teleoperational assembly at a third roll position between the first and second roll positions, wherein the sequence of images includes an image generated from the third image data.

20. The non-transitory machine-readable medium of claim 19, wherein the method further comprises rotating the image generated from the third image data.

21. The non-transitory machine-readable medium of claim 19, wherein the sequence of images includes a three-dimensional transition animation or a wipe transition animation.

* * * * *